United States Patent
Goda

(10) Patent No.: US 11,912,569 B2
(45) Date of Patent: Feb. 27, 2024

(54) METHOD FOR MANUFACTURING CHLOROUS ACID WATER USING RAW MATERIAL OBTAINED BY SALT ELECTROLYSIS

(71) Applicant: HONBUSANKEI CO., LTD., Osaka (JP)

(72) Inventor: Hisataka Goda, Osaka (JP)

(73) Assignee: HONBUSANKEI CO., LTD., Osaka (JP)

(*) Notice: Subject to any disclaimer, the term of this patent is extended or adjusted under 35 U.S.C. 154(b) by 437 days.

(21) Appl. No.: 16/088,708

(22) PCT Filed: Mar. 30, 2017

(86) PCT No.: PCT/JP2017/013333
§ 371 (c)(1),
(2) Date: Sep. 26, 2018

(87) PCT Pub. No.: WO2017/170904
PCT Pub. Date: Oct. 5, 2017

(65) Prior Publication Data
US 2020/0299133 A1 Sep. 24, 2020

(30) Foreign Application Priority Data
Mar. 31, 2016 (JP) .................. 2016-070264

(51) Int. Cl.
*C01B 11/08* (2006.01)
*C25B 1/26* (2006.01)
*C25B 15/02* (2021.01)

(52) U.S. Cl.
CPC .............. *C01B 11/08* (2013.01); *C25B 1/265* (2013.01); *C25B 15/02* (2013.01)

(58) Field of Classification Search
CPC ......... C01B 11/08; C25B 1/265; C25B 15/02; C02F 1/46; C02F 1/70; A61L 2/18
See application file for complete search history.

(56) References Cited

U.S. PATENT DOCUMENTS

| 2,797,192 A | 6/1957 | Graff et al. |
| 4,176,168 A | 11/1979 | Goto |
(Continued)

FOREIGN PATENT DOCUMENTS

| AU | 2015203851 A1 | 7/2015 |
| CA | 1109019 | 9/1981 |
(Continued)

OTHER PUBLICATIONS

Wikipedia entry on chloric acid.*
(Continued)

*Primary Examiner* — Salil Jain
(74) *Attorney, Agent, or Firm* — Renner, Otto, Boisselle & Sklar, LLP

(57) ABSTRACT

The present invention provides a method for manufacturing a chlorous acid aqueous solution using salt as a raw material. The present invention provides a method for manufacturing a chlorous acid aqueous solution, the method including 1) a step for electrolyzing salt and obtaining a chlorate or an aqueous solution thereof, and 2) a step for reducing the chlorate or aqueous solution thereof and manufacturing an aqueous solution including chlorous acid. The method for manufacturing a chlorous acid aqueous solution includes a step for mixing an inorganic acid or an inorganic acid salt as a simple substance or two or more types thereof with the aqueous solution including chlorous acid, and then mixing any of an inorganic acid, an inorganic acid salt, an organic acid, or an organic acid salt as a simple substance or two or more types thereof.

44 Claims, 3 Drawing Sheets

(56) References Cited

U.S. PATENT DOCUMENTS

| | | | |
|---|---|---|---|
| 4,250,003 A | | 2/1981 | Charvin et al. |
| 4,470,888 A | * | 9/1984 | Wheaton ................ C25B 1/265 |
| | | | 205/503 |
| 4,877,500 A | * | 10/1989 | Callerame ............. B01J 19/123 |
| | | | 204/157.48 |
| 5,378,447 A | * | 1/1995 | Jackson ................ C01B 11/023 |
| | | | 423/240 R |
| 8,951,576 B2 | * | 2/2015 | Goda ...................... A23L 3/358 |
| | | | 424/661 |
| 2010/0330202 A1 | | 12/2010 | Goda |
| 2013/0302438 A1 | * | 11/2013 | Goda ...................... C01B 11/08 |
| | | | 424/606 |
| 2016/0338391 A1 | | 11/2016 | Goda |

FOREIGN PATENT DOCUMENTS

| | | |
|---|---|---|
| CN | 1778396 A | 5/2006 |
| CN | 101348238 A | 1/2009 |
| CN | 101511192 A | 8/2009 |
| CN | 101878779 A | 11/2010 |
| CN | 105228655 A | 1/2016 |
| CN | 105263327 A | 1/2016 |
| JP | 55-69275 | 5/1980 |
| JP | 2005-330159 A | 12/2005 |
| JP | 2015-110544 | 6/2015 |
| WO | 03011750 A2 | 2/2003 |
| WO | WO 2008/026607 | 3/2008 |
| WO | 2014188310 A1 | 11/2014 |
| WO | WO 2014/188312 A2 | 11/2014 |
| WO | WO 2015/093062 A1 | 6/2015 |

OTHER PUBLICATIONS

Examination Report for counterpart Australian Application No. 2017245046 dated Feb. 14, 2020.
Office Action for counterpart Japanese Application No. 2018-509453 dated Nov. 1, 2019 and partial English translation.
Patent Examination Report No. 1 for counterpart Australian Application No. 2017245046 dated Sep. 25, 2019.
Office Action for counterpart Japanese Application No. 2018-509453 dated Jul. 29, 2020 and partial English translation.
International Search Report for related International Application No. PCT/JP2017/013333 dated Jun. 8, 2017.
Extended European Search Report for corresponding European Application No. 17775438.9 dated Nov. 20, 2019.
First Office Action for related Chinese Application No. 201760028159.6 dated Jun. 2, 2021 and it English translation.
Pre-Appeal Examination Report for related Japanese Application No. 2018-509453 dated Jan. 27, 2021 and partial English translation.
Second Office Action for related Chinese Application No. 201780028159.6 dated Jan. 5, 2022 and its English translation.
Office Action for related Japanese Application No. 2018-509453 dated Jun. 15, 2022 and its partial English translation.
Office Action for related Chinese Application No. 201780028159.6 dated Apr. 26, 2022 and its English translation.
Office Action for related Japanese Application No. 2020-15005 dated Jun. 15, 2022 and its partial English translation.
Additive Evaluation Report Chlorous Acid Aqueous Solution (Second edition), Jul. 2012, Food Safety Commission, [retrieved on Jun. 1, 2022], Internet<URL:https://www.fsc.go.jp/fsciis/attachedFile/download?retrievalId=kya20120402449&fileId=002> and partial English translation.
Final Office Action for related Japanese Application No. 2022-089681 dated Jun. 16, 2023.
First Office Action for related Japanese Application No. 2022-089681 dated Feb. 2, 2023 and machine translation.
Communication pursuant to Article 94(3) EPC for related European Patent Application No. 17775438.9 dated Jan. 9, 2023.

* cited by examiner

METHOD FOR MANUFACTURING CHLOROUS ACID WATER USING RAW MATERIAL OBTAINED BY SALT ELECTROLYSIS

TECHNICAL FIELD

The present invention relates to a method of manufacturing a chlorous acid aqueous solution using a raw material obtained by electrolyzing a salt.

BACKGROUND ART

A chlorous acid aqueous solution have drawn interest as an antimicrobial agent, sterilizing agent, microbe-removing agent, disinfecting agent, antiviral agent, and food additive/sterilizer.

The inventor has discovered chlorous acid aqueous solution and a method of manufacture thereof, have confirmed that it has a sterilizing effect to *E. coli*, and have filed the Patent Application (Patent Literature 1). Patent Literature 1 discloses the use of sodium chlorate as the raw material of a chlorous acid aqueous solution.

CITATION LIST

Patent Literature

[PTL 1] International Publication No. WO 2008/026607

SUMMARY OF INVENTION

Solution to Problem

As a result of diligent research on a novel method of manufacturing a chlorous acid aqueous solution in place of conventional methods using chlorate such as sodium chlorate as the raw material, the inventor has found a technology related to a method of manufacturing a chlorous acid aqueous solution using chlorate obtained by electrolysis of a salt that is cheaper and more stable than chlorate as the raw material. Although the method has one additional step of electrolysis compared to conventional methods, the method enables the manufacture of not only a chlorous acid aqueous solution with an antimicrobial effect, sterilizing effect, microbe-removing effect, disinfecting effect, and antiviral effect having conventional functions, but also a chlorous acid aqueous solution that also has a high antimicrobial power, sterilizing power, microbe-removing power, disinfecting power, and antiviral power.

The present invention also provides the following embodiments.

(Item 1)
A method of manufacturing a chlorous acid aqueous solution, including the steps of: 1) electrolyzing a salt to obtain a chlorate or an aqueous solution thereof; and 2) reducing the chlorate or the aqueous solution thereof to obtain an aqueous solution including a chlorous acid.

(Item 2)
The method of the preceding item, wherein the salt is sodium chloride.

(Item 3)
The method of any one of the preceding items, wherein the sodium chloride meets the specification of sodium chloride in the Japanese Pharmacopoeia or a specification equivalent thereto.

(Item 4)
The method of any one of the preceding items, wherein the chlorate or aqueous solution thereof includes at least about 45% (w/v) sodium chlorate, and optionally includes sodium hypochlorite or an unreacted substance.

(Item 5)
The method of any one of the preceding items, wherein the electrolyzing includes making an aqueous saturated sodium chloride solution flow in a diaphragm-free electrolytic cell and adjusting a pH of an electrolyte solution to about 5.9 to about 7.5 while conducting electricity for about 15 hours or more under conditions with a voltage of about 2.75 to about 3.5 V, a current density of about 600 to about 5000 $A/m^2$, and a solution temperature of about 70° C. to about 90° C.

(Item 6)
The method of any one of the preceding items, wherein the voltage is about 3V.

(Item 7)
The method of any one of the preceding items, wherein the current density is about 2500 $A/m^2$.

(Item 8)
The method of any one of the preceding items, wherein the pH of the electrolyte solution is adjusted to about 5.9 to about 7.0.

(Item 9)
The method of any one of the preceding items, wherein the pH of the electrolyte solution is adjusted to about 6.0.

(Item 10)
The method of any one of the preceding items, wherein at least one acid selected from the group consisting of sulfuric acid, phosphoric acid, and nitric acid is used in the reducing step.

(Item 11)
The method of any one of the preceding items, wherein a concentration of the sulfuric acid, phosphoric acid, or nitric acid is about 60% (w/w) to about 90% (w/w).

(Item 12)
The method of any one of the preceding items, wherein the concentration of the sulfuric acid, phosphoric acid, or nitric acid is about 70% (w/w).

(Item 13)
The method of any one of the preceding items, wherein the acid includes an acidic thiosulfuric acid or a salt thereof.

(Item 14)
The method of any one of the preceding items, wherein a concentration of the acidic thiosulfuric acid is about 0% (w/v) to about 1.3% (w/v).

(Item 15)
The method of any one of the preceding items, wherein the concentration of the acidic thiosulfuric acid is about 0.5% (w/v) to about 0.7% (w/v).

(Item 16)
The method of any one of the preceding items, including the step of obtaining a gasified substance including a chlorous acid.

(Item 17)
The method of any one of the preceding items, wherein an oxyacid with a reducing action is used concurrently in the reducing step.

(Item 18)
The method of any one of the preceding items, wherein the oxyacid with a reducing action is acidic thiosulfuric acid, dithionous acid, peroxymonosulfuric acid, peroxydisulfuric acid, peroxyphosphoric acid, peroxychromic acid, or manganese oxide.

(Item 19)
The method of any one of the preceding items, wherein the oxyacid with a reducing action is acidic thiosulfuric acid or dithionous acid.
(Item 20)
The method of any one of the preceding items, wherein the oxyacid with a reducing action is generated from a salt of the oxyacid with a reducing action in the reducing step.
(Item 21)
The method of any one of the preceding items, wherein the salt of the oxyacid with a reducing action is acidic thiosulfate, dithionite, peroxymonosulfate, peroxydisulfate, peroxyphophate, peroxychromate, or permanganate.
(Item 22)
The method of any one of the preceding items, wherein the salt of the oxyacid with a reducing action is sodium dithionite or sodium thiosulfate.
(Item 23)
The method of any one of the preceding items, wherein the oxyacid with a reducing action is used concurrently with hydrogen peroxide.
(Item 24)
The method of any one of the preceding items, wherein the oxyacid with a reducing action is acidic thiosulfuric acid or dithionous acid, wherein a concentration of the acidic thiosulfuric acid or dithionous acid is about 0.5% to about 1.5% when the acidic thiosulfuric acid or dithionous acid is used concurrently with hydrogen peroxide.
(Item 25)
The method of any one of the preceding items, wherein the concentration of the acidic thiosulfuric acid or dithionous acid is about 0.5% to about 1.0%.
(Item 26)
The method of any one of the preceding items, including the step of generating a first reaction gas using the acid and the oxyacid with a reducing action in step 2).
(Item 27)
The method of any one of the preceding items, including the step of generating a second reaction gas using hydrogen peroxide and the oxyacid with a reducing action in step 2).
(Item 28)
The method of any one of the preceding items, including the step of capturing the first reaction gas in an aqueous solution including a chlorous acid using a neutralization agent in step 2).
(Item 29)
The method of any one of the preceding items, including the step of capturing the second reaction gas in an aqueous solution including a chlorous acid using a neutralization agent in step 2).
(Item 30)
The method of any one of the preceding items, wherein a pH of the neutralization agent is about 6.0 or greater.
(Item 31)
The method of any one of the preceding items, wherein the pH of the neutralization agent is about 10.3 to about 10.7.
(Item 32)
The method of any one of the preceding items, wherein a TAL of the neutralization agent is about 20 or greater.
(Item 33)
The method of any one of the preceding items, wherein a TAL of the neutralization agent is about 2000.
(Item 34)
The method of any one of the preceding items, wherein the neutralization agent has a high buffering power in a pH range of about 4.5 to about 7.5.
(Item 35)
The method of any one of the preceding items, wherein the neutralization agent includes any one of an inorganic acid, an inorganic acid salt, an organic acid, and an organic acid salt, or two or more types thereof.
(Item 36)
The method of any one of the preceding items, including the step of mixing any one of an inorganic acid, an inorganic acid salt, an organic acid, and an organic acid salt, or two or more types thereof, into the aqueous solution including the chlorous acid.
(Item 37)
The method of any one of the preceding items, including the step of mixing any one of an inorganic acid and an inorganic acid salt, or two or more types thereof, into the aqueous solution including the chlorous acid.
(Item 38)
The method of any one of the preceding items, including the step of mixing any one of an inorganic acid and an inorganic acid salt, or two or more types thereof, into the aqueous solution including the chlorous acid, and then mixing any one of an inorganic acid, an inorganic acid salt, an organic acid, and an organic acid salt or two or more types thereof.
(Item 39)
The method of any one of the preceding items, characterized in that the inorganic acid is carbonic acid, phosphoric acid, boric acid, or sulfuric acid.
(Item 40)
The method of any one of the preceding items, characterized in that the inorganic acid salt is carbonate, hydroxide salt, phosphate, or borate.
(Item 41)
The method of any one of the preceding items, characterized in that the carbonate is sodium carbonate, potassium carbonate, sodium bicarbonate, or potassium bicarbonate.
(Item 42)
The method of any one of the preceding items, characterized in that the hydroxide salt is sodium hydroxide or potassium hydroxide.
(Item 43)
The method of any one of the preceding items, characterized in that the phosphate is disodium hydrogen phosphate, sodium dihydrogen phosphate, trisodium phosphate, tripotassium phosphate, dipotassium hydrogen phosphate, or potassium dihydrogen phosphate.
(Item 44)
The method of any one of the preceding items, characterized in that the borate is sodium borate or potassium borate.
(Item 45)
The method of any one of the preceding items, characterized in that the organic acid is succinic acid, citric acid, malic acid, acetic acid, or lactic acid.
(Item 46)
The method of any one of the preceding items, characterized in that the organic acid salt is sodium succinate, potassium succinate, sodium citrate, potassium citrate, sodium malate, potassium malate, sodium acetate, potassium acetate, sodium lactate, potassium lactate, or calcium lactate.
(Item 47)
A chlorous acid aqueous solution produced by the method of any one of the preceding items.
(Item 48)
An apparatus for manufacturing a chlorous acid aqueous solution, including 1) an electrolytic cell for electrolyzing a salt to obtain a chlorate or an aqueous solution thereof, and
2) a reaction tank for reducing the chlorate or an aqueous solution thereof to obtain an aqueous solution including a chlorous acid.
(Item 49)
An agent for adjusting reactivity of a chlorous acid aqueous solution including an oxyacid with a reducing action.

The present invention is intended so that one or more of the features can be provided not only as the explicitly disclosed combinations, but also as other combinations thereof. Additional embodiments and advantages of the present invention are recognized by those skilled in the art by reading and understanding the following detailed description as needed.

Advantageous Effects of Invention

The present invention provides a novel method of manufacturing a useful agent, i.e., chlorous acid aqueous solution, by using an electrolyzed salt, i.e., chlorate. This has further increased the possibility of wide utilization in an antimicrobial, sterilizing, microbe-removing, disinfecting, and antiviral use in the food industry, medical setting, nursing and day care, education field, other consumable items, and the like.

The method of manufacturing a chlorous acid aqueous solution of the present invention, compared to conventional manufacturing methods described in Patent Literature 1,
(1) is safer because chlorate is never directly handled as the raw material,
(2) uses a salt with a lower cost as the raw material, and
(3) directly uses a reaction solution obtained in an electrolysis reaction in a subsequent step, thus enabling the manufacture of not only chlorous acid aqueous solutions with a chlorous acid as the primary active ingredient, but also chlorous acid aqueous solutions with various functions.

Regarding (1), since chlorate such as sodium chlorate is designated as a category I hazardous material under the Fire Service Act and a deleterious substance under the Poisonous and Deleterious Substances Control Act and is a potent oxidant, chlorate is a substance that cannot be readily handled, requiring care in handling, because it was necessary to store chlorate away from organic compounds and substances that are readily oxidized. Meanwhile, the manufacturing method of the present invention generates chlorate in an electrolysis reaction system and directly transitions to the next step, so that a chlorous acid aqueous solution can be manufactured more safely compared to conventional manufacturing methods.

Regarding (2), the manufacturing method of the present invention uses sodium chloride that meets the specification of sodium chloride in the Japanese Pharmacopoeia. This is for preventing the generation of a carcinogenic substance bromic acid ($BrO_3-$) from bromide ($Br-$) since salt is used as the raw material. Although not wishing to be bound by any theory, the amount of bromic acid ($BrO_3-$) generated can be kept below the water quality standards for drinking water by using sodium chloride meeting the specification of sodium chloride in the Japanese Pharmacopoeia (bromide ($Br-$) concentration: 100 µg/g or less).

Regarding (3), a chloric acid containing aqueous solution generated in an electrolysis reaction system using sodium chloride that meets the specification of sodium chloride in the Japanese Pharmacopoeia as a raw material is used directly in the next manufacturing step. Thus, not only a chlorous acid aqueous solution primarily with a delayed effect, which was manufacturable with a conventional manufacturing patent, but also chlorous acid aqueous solutions with various functions such as significantly improved high reactivity can be manufactured by concurrent use of oxyacid with a reducing action such as acidic thiosulfuric acid or dithionous acid, while a reducing agent was limited to hydrogen peroxide in the past.

DESCRIPTION OF EMBODIMENTS

Figure 1:
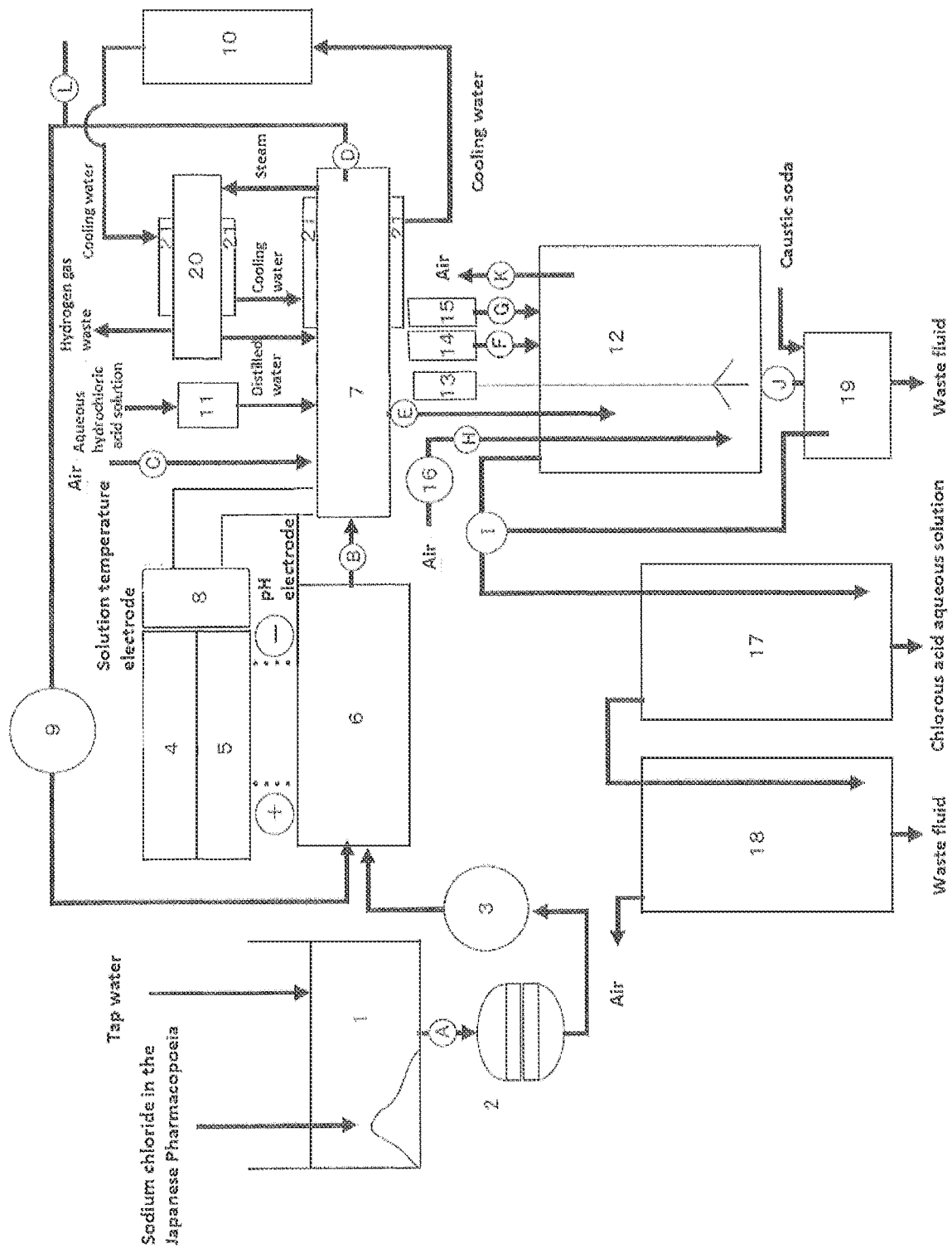
FIG. 1 depicts a schematic diagram of a manufacturing plant, in which a diaphragm free electrolytic cell and mixing tank for each solution are separated. 1: salt dissolving tank, 2: saturated salt water filtration apparatus, 3: pump 1, 4: control panel, 5: rectifier/power source, 6: electrolytic cell, 7: storage tank, 8: measurement instrument, 9: pump 2, 10: cooling apparatus, 11: hydrochloric acid titration apparatus, 12: reaction tank, 13: stirring apparatus, 14: acid adding instrument, 15: hydrogen peroxide adding instrument, 16: pump 3, 17: neutralization tank, 18: gas washing tank, 19: waste fluid treating tank, 20: capacitor, 21: jacket, A: saturated salt water discharge valve, B: electrolytic cell discharge valve, C: air valve, D: circulation opening/closing spigot, E: liquor discharge valve, F: sulfuric acid inlet valve, G: hydrogen peroxide inlet valve, H: air pump spigot, I: trifurcated spigot, J: reaction solution discharge valve, K: air valve, L: sample valve.
Figure 2:
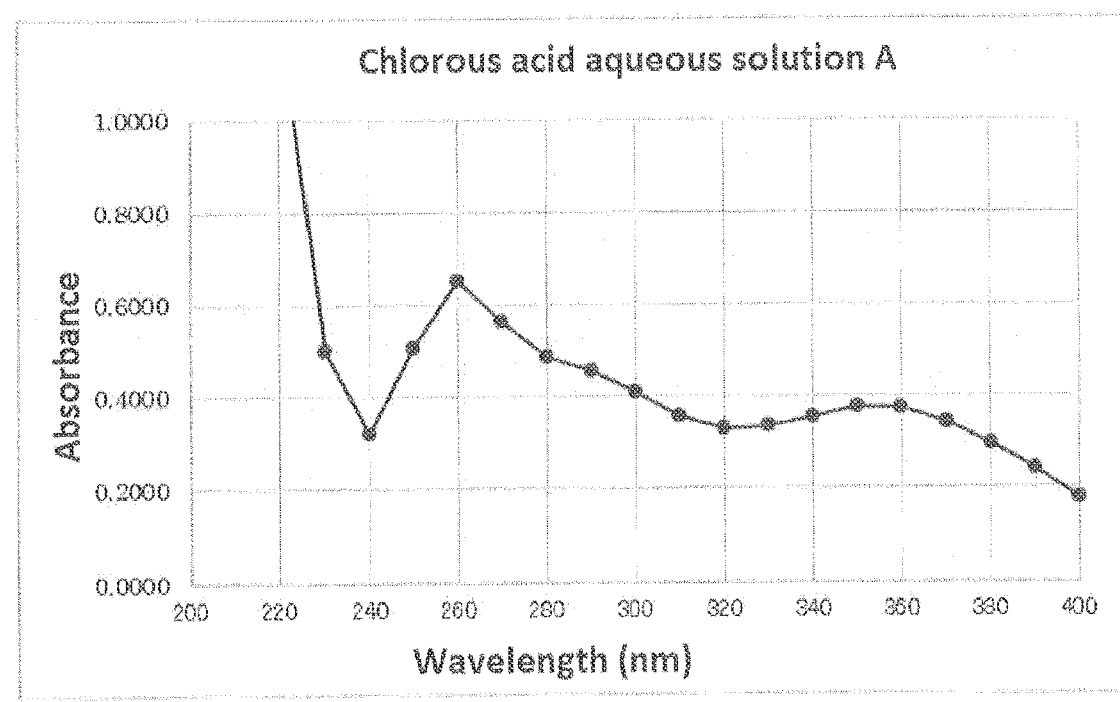
FIG. 2 shows the UV spectra of chlorous acid aqueous solution A. The vertical axis indicates the absorbance, and the horizontal axis indicates the wavelength (nm).
Figure 3:
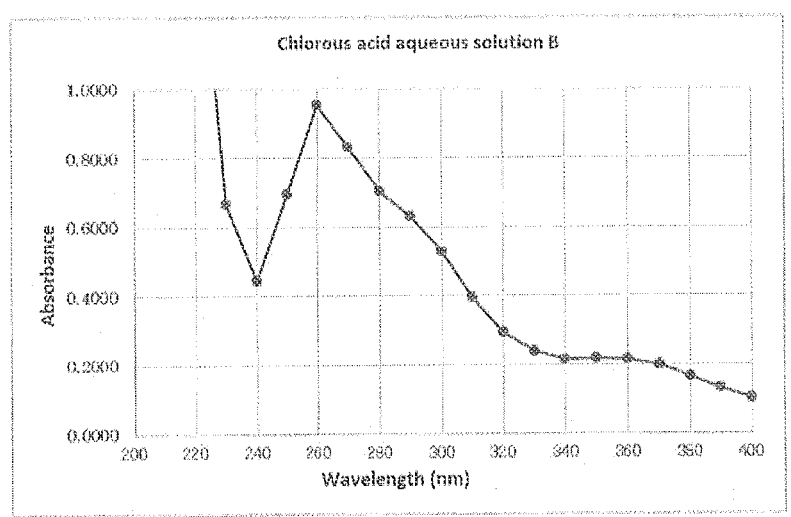
FIG. 3 shows the UV spectra of chlorous acid aqueous solution B. The vertical axis indicates the absorbance, and the horizontal axis indicates the wavelength (nm).

The present invention is described hereinafter while showing the best mode of the invention. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definitions of the Terms

The terms used herein are described hereinafter.

As used herein, "chlorous acid aqueous solution" refers to an aqueous solution including chlorous acid ($HClO_2$), which is used as an antimicrobial agent, sterilizing agent, microbe-removing agent, disinfecting agent, antiviral agent, and food additive: sterilizer. The chlorous acid aqueous solution of the present invention creates a transitional state and delays a decomposition reaction, so that chlorous acid ($HClO_2$) can be stably maintained over a long period of time. When a sample of chlorous acid aqueous solution is measured with a spectrophotometer, the presence of chlorous acid can be indirectly confirmed when an absorbent section including a dissociated chlorous acid ($H^+ \cdot ClO_2^-$) representing a peak near 260 nm and an absorbent section including aqueous chlorine dioxide ($ClO_2$ in water phase) representing a peak near 350 nm can be simultaneously observed between wavelengths of 240 to 420 nm in the UV spectrum, i.e., when a double peak is exhibited. In such a case, it is understood that a cyclic reaction primarily involving the equilibrium ($HClO_2 <-> H^+ \cdot ClO_2^-$) of chlorous acid ($HClO_2$) and dissociated chlorous acid ($H^+ \cdot ClO_2^-$) where an electron of an acidic aqueous solution is received and returned to the dissociated chlorous acid ($H^+ \cdot ClO_2^-$) via aqueous chlorine dioxide ($ClO_2$ in water phase) is simultaneously in progress.

As used herein, the term "chlorous acid aqueous solution" can encompass a "chlorous acid aqueous solution preparation". A chlorous acid aqueous solution preparation can be manufactured by using a chlorous acid aqueous solution manufactured through the manufacturing method of the present invention and adding a specific buffer. As a representative constitution of a chlorous acid aqueous solution preparation, 14.500% (w/v) chlorous acid aqueous solution (4% product), 1.000% (w/v) potassium dihydrogen phosphate, 0.014% (w/v) sodium hydroxide, and 86.500% (w/v) purified water can be mixed and used (sold under the name "Keaforupisu" by the Applicant), but the constitution is not limited thereto. For this formulation constitution, the chlorous acid aqueous solution may be 0.25% (w/v) to 75% (w/v), potassium dihydrogen phosphate may be 0.70% (w/v) to 13.90% (w/v), and sodium hydroxide may be 0.01% (w/v) to 5.60% (w/v). It is also possible to use sodium dihydrogen phosphate instead of potassium dihydrogen phosphate, and potassium hydroxide instead of sodium hydroxide.

As used herein, "stability" of a chlorous acid aqueous solution refers to a state of maintaining chlorous acid ($HClO_2$).

As used herein, "antimicrobial (action)" refers to suppression of growth of pathogenic, harmful, or infectious microorganisms such as mold and microbes. A substance having antimicrobial action is referred to as an antimicrobial agent.

As used herein, "sterilizing (action)" refers to killing of pathogenic, harmful, or infectious microorganisms such as mold and microbes. A substance having sterilizing action is referred to as a sterilizing agent.

As used herein, "microbe-removing (action)" refers to removal of pathogenic, harmful, or infectious microorganisms such as mold and microbes. A substance having microbe-removing action is referred to as a microbe-removing agent.

As used herein, "disinfecting (action)" refers to disinfection of pathogenic, harmful, or infectious microorganisms such as mold and microbes. A substance having disinfecting action is referred to as a disinfecting agent.

As used herein, "antiviral (action)" refers to inactivation of a virus or the like. A substance having an inactivation effect (action) is referred to as an antiviral agent.

A substance with an antimicrobial action is referred to as an antimicrobial agent, a substance with a sterilizing action is referred to as a sterilizing agent, a substance with a microbe-removing action is referred to as a microbe-removing agent, a substance with a disinfecting action is referred to as a disinfecting agent, and a substance with an antiviral action is referred to as an antiviral agent, which need to be distinctly expressed herein. Substances that are not described herein do not fall under them. As used herein, these terms are generally understood as agents that also have action corresponding to antimicrobial action, sterilizing action, microbe-removing action, disinfecting action, and virus inactivation action.

As used herein, an article used with a manufactured chlorous acid aqueous solution is any article that can be impregnated with the chlorous acid aqueous solution to be used for antimicrobial action, sterilizing action, microbe-removing action, disinfecting action, and virus inactivation action purposes, including medical devices and the like. Examples thereof include, but are not limited to, a sheet, film, patch, brush, nonwoven fabric, paper, fabric, absorbent cotton, sponge, and the like. Any material may be used, as long as a chlorous acid aqueous solution can be impregnated therein.

As used herein, "TAL" is used to measure alkalinity of a sample by titrating 0.1 mol/L hydrochloric acid-standard acid solution until the sample has a pH of 4.0, wherein alkalinity (TAL) is 1 when 1 mL of 0.1 mol/L hydrochloric acid is required to make 100 g of sample to have a pH of 4.0. A pH of 4.0 is the second neutralization point for sodium carbonate. Since high test hypochlorite has a broad specification and varies between manufacturers depending on the formulation of the pH adjuster or the like, TAL is generally not described in the specification in many cases.

As used herein, "oxyacid with a reduction action" refers to an acid in which hydrogen that can dissociate as a proton is bound to an oxygen atom, represented by the general formula $XO_n(OH)_m$ (wherein X is a metal atom or a non-metal atom other than oxygen, and n and m are integers that are 1 or greater). Representative examples of oxyacids with a reducing action include thiosulfuric acid, dithionous acid, peroxymonosulfuric acid, peroxydisulfuric acid, and the like.

As used herein, "liquor" refers to a liquid generated after electrolysis (see John J. McKetta, Guy E. Weismantel, editor, "Encyclopedia of Chemical Processing and Design", pages 51 and 148 to 151).

As used herein, "acidic thiosulfuric acid" refers to "thiosulfate in an acidic state", which is obtained from thiosulfuric acid by adding thiosulfate to a strong acidic substance such as sulfuric acid.

When a numerical value is preceded by the term "about" herein, the numerical value indicates a range of numerical values that result in the described value when the number one digit below is rounded. For example, it is understood that about 5 means 4.5 to less than 5.5, and about 0.5 means 0.45 to less than 0.55.

(Chlorous Acid Aqueous Solution and Manufacturing Example Thereof)

The chlorous acid aqueous solution used in the present invention has the features and functions found by the inventor.

The present invention relates to a method that is different from known manufacturing methods, such as those described in Patent Literature 1.

In other words, conventional manufacturing methods of chlorous acid aqueous solutions adds and reacts an aqueous solution of sodium chlorate, which has a strong oxidizing action and a property of inducing an explosion from heat, friction or impact when mixed with an organic matter, sulfur, metal powder or the like, with sulfuric acid or an aqueous solution thereof at an amount and concentration that can maintain the pH of the aqueous solution within 2.3 to 3.4 to generate chloric acid, and adds hydrogen peroxide at an amount that is equal to or greater than the amount required for a reducing reaction of the chloric acid. It is known that a chlorous acid aqueous solution obtained by this manufacturing method forms a "cyclic reaction" that can indirectly maintain unstable chlorous acid and has a function of supplementing the oxidation capability that has been lost by contact with an organic matter or microorganism so that the same antimicrobial power, sterilizing power, microbe-removing power, disinfecting power, and antiviral power can be maintained indefinitely, which is a feature that is clearly different from the antimicrobial effect, sterilizing effect, microbe-removing effect, disinfecting effect, and antiviral effect of sodium hypochlorite that are strong effects but immediately disappear upon contact with an organic matter or a microorganism.

Meanwhile, the present invention electrolyzes a salt that has a low cost and is readily handled instead of chlorate as the raw material to obtain chlorate or an aqueous solution including chlorate and then adds dithionous acid or acidic thiosulfuric acid, which is acidified with sulfuric acid, to the aqueous solution to perform a first reaction. At this time, chlorine gas including a chlorous acid is generated, and then hydrogen peroxide mixed with acidic thiosulfuric acid, dithionous acid, or the like is further added to perform a second reaction. At this time, chlorine dioxide gas including a chlorous acid is generated, and each gas is allowed to adsorb to a neutralization agent with high TAL and buffering power in the neutral region. Optionally, the gas generated in the first reaction and the gas generated in the second reaction can be allowed to adsorb to separate neutralization agents and then combined. Development of a method of manufacturing a chlorous acid aqueous solution with various functions such as high reactivity compared to conventional manufacturing methods is achieved by adding a buffer as needed to a chlorous acid aqueous solution prepared by allowing the first reaction gas and the second reaction gas to adsorb to maintain the pH (pH 3.2 to pH 8.5).

DESCRIPTION OF PREFERRED EMBODIMENTS

Preferred embodiments of the present invention are described hereinafter. It is understood that the embodiments provided hereinafter are provided to better facilitate understanding of the present invention, so that the scope of the present invention should not be limited by the following description. Thus, it is apparent that those skilled in the art can refer to the description herein to make appropriate modifications within the scope of the present invention. It is also understood that the following embodiments of the present invention can be used alone or in combination.

In one aspect, the present invention provides a method of manufacturing a chlorous acid aqueous solution, including the steps of: 1) electrolyzing a salt to obtain a chlorate or an aqueous solution thereof; and (2) reducing the chlorate or the aqueous solution thereof to manufacture an aqueous solution including a chlorous acid. The present invention preferably provides a method of manufacturing a chlorous acid aqueous solution, including the steps of: 1) electrolyzing a salt to obtain a chlorate or an aqueous solution thereof; and (2) reducing the chlorate or the aqueous solution thereof by concurrently using one or several types of oxyacids with a reducing action to manufacture an aqueous solution including a chlorous acid. Although not wishing to be bound by any theory, this is because such a method enables the manufacture of a chlorous acid aqueous solution with better versatility compared to conventional methods using chlorate such as sodium chlorate as the raw material.

Conventional methods of manufacturing an aqueous solution including a chlorous acid ($HClO_2$) (chlorous acid aqueous solution), which can be used as an antimicrobial agent, sterilizing agent, microbe-removing agent, disinfecting agent, and an antiviral agent, generate chlorous acid ($HClO_2$) by adding hydrogen peroxide ($H_2O_2$) in an amount required to produce chlorous acid by a reducing reaction from chloric acid ($HClO_3$) obtained by adding sulfuric acid ($H_2SO_4$) or an aqueous solution thereof to an aqueous solution of sodium chlorate ($NaClO_3$) to induce an acidic condition. The basic chemical reaction of this method of manufacturing is represented by the following formula A and formula B.

[Chemical 1]

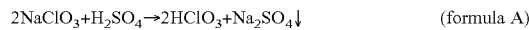
$$2NaClO_3 + H_2SO_4 \rightarrow 2HClO_3 + Na_2SO_4 \downarrow \qquad \text{(formula A)}$$

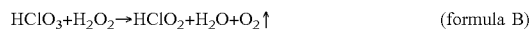
$$HClO_3 + H_2O_2 \rightarrow HClO_2 + H_2O + O_2 \uparrow \qquad \text{(formula B)}$$

Formula A indicates that chloric acid is obtained while sodium ions are simultaneously removed by adding sulfuric acid ($H_2SO_4$) or an aqueous solution thereof in an amount and concentration at which the pH value of an aqueous sodium chlorate ($NaClO_3$) solution can be maintained within acidity. Next, formula B indicates that chloric acid ($HClO_3$) is reduced with hydrogen peroxide ($H_2O_2$) to produce chlorous acid ($HClO_2$).

[Chemical 2]

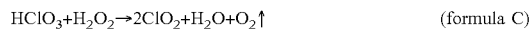
$$HClO_3 + H_2O_2 \rightarrow 2ClO_2 + H_2O + O_2 \uparrow \qquad \text{(formula C)}$$

$$2ClO_2 + H_2O_2 \rightarrow 2HClO_2 + O_2 \uparrow \qquad \text{(formula D)}$$

$$2ClO_2 + H_2O \leftrightarrow HClO_2 + HClO_3 \qquad \text{(formula E)}$$

$$2HClO_2 \leftrightarrow H_2O + Cl_2O_3 \qquad \text{(formula F)}$$

At this time, chlorine dioxide gas ($ClO_2$) is generated (formula C). However, coexistence with hydrogen peroxide ($H_2O_2$) results in the production of chlorous acid ($HClO_2$) through the reactions in formulas D-F. Conventional inventions utilize the reactions after the chlorine dioxide gas ($ClO_2$).

In this regard, the method of manufacturing a chlorous acid aqueous solution in the present invention starts from electrolyzing a salt into a raw material. This reaction is a known method, which is performed according to formula G

$$NaCl + 3H_2O \rightarrow NaClO_3 + 3H_2 \qquad \text{(formula G)}.$$

However, if the pH condition is not optimal or if the current density upon electricity conduction cannot be sufficiently supplied, a reaction specified in formula H can also occur as a side reaction.

$$NaCl + H_2O \rightarrow NaClO + H_2 \qquad \text{(formula H)}$$

In one preferred embodiment, the salt is sodium chloride. Although not wishing to be bound by any theory, this is because a chlorous acid aqueous solution can be safely manufactured by using sodium chloride as a raw material.

In a more preferred embodiment, the sodium chloride meets the specification of sodium chloride in the Japanese Pharmacopoeia. Although not wishing to be bound by any theory, this is because the amount of bromic acid ($BrO_3-$) generated can be kept at or below the water quality standards for drinking water by using only sodium chloride meeting the specification of sodium chloride in the Japanese Pharmacopoeia (bromide (Br—) concentration: 100 µg/g or less).

In a preferred embodiment, the electrolyzing includes making an aqueous saturated sodium chloride solution flow in a diaphragm-free electrolytic cell and adding about 0.3% hydrochloric acid (approximately 0.1N—HCl) and conducting electricity to maintain a pH region of about 5.9 to about 7.5.

Examples of preferred pH upon electrolysis include, but are not limited to, a pH region of about 5.9 to about 7.5, about 6.0 to about 7.5, about 6.1 to about 7.5, about 6.2 to about 7.5, about 6.3 to about 7.5, about 6.4 to about 7.5, about 6.5 to about 7.5, about 6.6 to about 7.5, about 6.7 to about 7.5, about 6.8 to about 7.5, about 6.9 to about 7.5, about 7.0 to about 7.5, about 7.1 to about 7.5, about 7.2 to about 7.5, about 7.3 to about 7.5, and about 7.4 to about 7.5. Examples of more preferred pH include, but are not limited to, a pH region of about 5.9 to about 7.5. Examples of still more preferred pH include, but are not limited to, pH region of about 5.9 to about 7.0. The most preferred examples of pH include, but are not limited to, about 6.0.

The conditions for electrolysis are electrical conduction under conditions with a voltage of about 2.75 to about 3.5 V, a current density of about 600 to about 5000 $A/m^2$, and a solution temperature of about 70° C. to about 90° C. Although not wishing to be bound by any theory, sodium chlorate with a relatively high purity is obtained, which, as a result, enables obtaining a chlorous acid aqueous solution equivalent to those obtained by a conventional manufacturing method such as those in Patent Literature 1.

Examples of a preferred voltage include, but are not limited to, about 2.8 to about 3.5 V, about 2.9 to about 3.5 V, about 3.0 to about 3.5V, about 3.1 to about 3.5 V, about 3.2 to about 3.5 V, about 3.3 to about 3.5 V, and about 3.4 to about 3.5 V. Examples of the most optimal voltage include, but are not limited to, about 3V.

Examples of preferred current density include, but are not limited to, about 600 to about 5000 $A/m^2$, about 700 to about 5000 $A/m^2$, about 800 to about 5000 $A/m^2$, about 900 to about 5000 $A/m^2$, about 1000 to about 5000 $A/m^2$, about 1100 to about 5000 $A/m^2$, about 1200 to about 5000 $A/m^2$, about 1300 to about 5000 $A/m^2$, about 1400 to about 5000 $A/m^2$, about 1500 to about 5000 $A/m^2$, about 1600 to about 5000 $A/m^2$, about 1700 to about 5000 $A/m^2$, about 1800 to about 5000 $A/m^2$, about 1900 to about 5000 $A/m^2$, about 2000 to about 5000 $A/m^2$, about 2100 to about 5000 $A/m^2$, about 2200 to about 5000 $A/m^2$, about 2300 to about 5000 $A/m^2$, about 2400 to about 5000 $A/m^2$, about 2500 to about 5000 $A/m^2$, about 600 to about 5000 $A/m^2$, about 600 to about 4900 $A/m^2$, about 600 to about 4800 $A/m^2$, about 600 to about 4700 $A/m^2$, about 600 to about 4600 $A/m^2$, about 600 to about 4500 $A/m^2$, about 600 to about 4400 $A/m^2$, about 600 to about 4300 $A/m^2$, about 600 to about 4200 $A/m^2$, about 600 to about 4100 $A/m^2$ about 600 to about 4000 $A/m^2$, about 600 to about 3900 $A/m^2$ about 600 to about 3800 $A/m^2$, about 600 to about 3700 $A/m^2$, about 600 to about 3600 $A/m^2$, about 600 to about 3500 $A/m^2$, about 600 to about 3400 $A/m^2$, about 600 to about 3300 $A/m^2$, about 600 to about 3200 $A/m^2$, about 600 to about 3100 $A/m^2$, about 600 to about 3000 $A/m^2$, about 600 to about 2900 $A/m^2$, about 600 to about 2800 $A/m^2$, about 600 to about 2700 $A/m^2$ about 600 to about 2600 $A/m^2$, and about 600 to about 2500 $A/m^2$. Examples of the most optimal current density include, but are not limited to, about 2500 $A/m^2$.

Under the conditions of about 70° C. to about 90° C., examples of preferred solution temperature include, but are not limited to, about 75° C. to about 90° C., about 80° C. to about 90° C., about 85° C. to about 90° C., about 70° C. to about 85° C., about 70° C. to about 80° C., and about 70° C. to about 75° C.

The concentration of the sulfuric acid, phosphoric acid, or nitric acid is, but not limited to, about 60% (w/w) to about 90% (w/w), more preferably about 65% (w/w) to about 90% (w/w), about 70% (w/w) to about 90% (w/w), about 60% (w/w) to about 85% (w/w), about 60% (w/w) to about 80% (w/w), or about 60% (w/w) to about 75% (w/w) and still more preferably about 70% (w/w).

The acid solution includes an acidic thiosulfuric acid. Although not wishing to be bound by any theory, this is because a chlorous acid aqueous solution with a more significantly improved high reactivity compared to conventional chlorous acid aqueous solutions can be manufactured when an acid solution includes acidic thiosulfuric acid.

The concentration of the acidic thiosulfuric acid is not limited to, but is preferably about 0% (w/v) to about 1.3% (w/v), more preferably about 0.1% (w/v) to about 1.3% (w/v), about 0.2% (w/v) to about 1.3% (w/v), about 0.3% (w/v) to about 1.3% (w/v), about 0.4% (w/v) to about 1.3% (w/v), about 0.5% (w/v) to about 1.3% (w/v), about 0% (w/v) to about 1.2% (w/v), about 0% (w/v) to about 1.1% (w/v), about 0% (w/v) to about 1.0% (w/v), about 0% (w/v) to about 0.9% (w/v), about 0% (w/v) to about 0.8% (w/v), or about 0% (w/v) to about 0.7% (w/v), and still more preferably about 0.5% (w/v) to about 0.7% (w/v).

In a preferred embodiment, an oxyacid with a reducing action or a salt thereof is used concurrently in the reducing step. Although not wishing to be bound by any theory, this is because concurrent use of oxyacid with a reducing action or a salt thereof in the reducing step enables the manufacture of not only conventional chlorous acid aqueous solutions primarily with a delayed effect, but also chlorous acid aqueous solutions with various functions such as significantly improved fast acting high reactivity. As a reducing agent used in the reducing step, hydrogen peroxide is generally used, and oxyacid with a reducing action is also used or concurrently used.

In a preferred embodiment, an oxyacid including hydrogen peroxide includes, besides hydrogen peroxide, dithionous acid, acidic thiosulfuric acid, peroxymonosulfuric acid, peroxydisulfuric acid, peroxyphosphoric acid, peroxychromic acid, or manganese oxide as an oxyacid with a reducing action. Although not wishing to be bound by any theory, this is because a conventional reducing reaction using hydrogen peroxide only generates chlorine dioxide, but a chlorous acid can be generated and gas including chlorous acid can be obtained by concurrent use of hydrogen peroxide with such an oxyacid with a reducing action. Examples of preferred oxyacids with a reducing action include, but are not limited to, acidic thiosulfuric acid and dithionous acid.

When the oxyacid with a reducing action is acidic thiosulfuric acid or dithionous acid and the acidic thiosulfuric acid or dithionous acid is concurrently used with hydrogen peroxide, the concentration of the acidic thiosulfuric acid or dithionous acid is, but not limited to, about 0.5% to about 1.5%, preferably about 0.5% to about 1.4%, about 0.5% to about 1.3%, about 0.5% to about 1.2%, about 0.5% to about 1.1%, or about 0.5% to about 1.0%, and still more preferably about 0.5% to about 1.0%.

The present manufacturing method generates two types of gas. Gas including chlorine and chlorous acid is obtained as gas from a first reaction (hereinafter, referred to as the first reaction gas) and gas including chlorous acid and chlorine dioxide is obtained as gas from a second reaction (hereinafter, referred to as the second reaction gas).

In a preferred embodiment, the pH of a neutralization agent allowing adsorption of first reaction gas and second reaction gas is not limited to, but is preferably about 6.0 or greater, about 6.5 or greater, about 7.0 or greater, about 7.5 or greater, about 8.0 or greater, about 8.5 or greater, about 9.0 or greater, about 9.5 or greater, about 10.0 or greater, about 11.0 or greater, about 12.0 or greater, or about 13.0 or greater, if possible about 6.0 or greater and about 11.0 or less, more preferably about 6.5 or greater and about 11.0 or less, about 7.0 or greater and about 11.0 or less, about 7.5 or greater and about 11.0 or less, about 8.0 or greater and about 11.0 or less, about 8.5 or greater and about 11.0 or less, about 9.0 or greater and about 11.0 or less, about 9.5 or greater and about 11.0 or less, about 10.0 or greater and about 11.0 or less, or about 10.5 or greater and about 11.0 or less, and optimally about 10.3 to about 10.7. TAL is about 20 or greater, about 30 or greater, about 40 or greater, about 50 or greater, about 60 or greater, about 70 or greater, about 80 or greater, about 90 or greater, about 100 or greater, about 200 or greater, about 300 or greater, about 400 or greater, about 500 or greater, about 600 or greater, about 700 or greater, about 800 or greater, about 900 or greater, about 1000 or greater, about 1100 or greater, about 1200 or greater, about 1300 or greater, about 1400 or greater, about 1500 or greater, about 1600 or greater, about 1700 or greater, about 1800 or greater, or about 1900 or greater, and optimally 2000, but is not limited thereto. Further, a neutralization agent with a high buffering power in the pH range of about 4.5 or greater and about 7.5 or less, about 4.6 or greater and about 7.5 or less, about 4.7 or greater and about 7.5 or less, about 4.8 or greater and about 7.5 or less, about 4.9 or greater and about 7.5 or less, about 5.0 or greater and about 7.5 or less, about 5.1 or greater and about 7.5 or less, about 5.2 or greater and about 7.5 or less, about 5.3 or greater and about 7.5 or less, about 5.4 or greater and about 7.5 or less, about 5.5 or greater and about 7.5 or less, about 5.6 or greater and about 7.5 or less, about 5.7 or greater and about 7.5 or less, about 5.8 or greater and about 7.5 or less, about 5.9 or greater and about 7.5 or less, about 6.0 or greater and about 7.5 or less, about 6.1 or greater and about 7.5 or less, about 6.2 or greater and about 7.5 or less, about 6.3 or greater and about 7.5 or less, about 6.4 or greater and about 7.5 or less, about 6.5 or greater and about 7.5 or less, about 6.6 or greater and about 7.5 or less, about 6.7 or greater and about 7.5 or less, about 6.8 or greater and about 7.5 or less, about 6.9 or greater and about 7.5 or less, about 7.0 or greater and about 7.5 or less, about 7.1 or greater and about 7.5 or less, about 7.2 or greater and about 7.5 or less, about 7.3 or greater and about 7.5 or less, about 7.4 or greater and about 7.5 or less, about 4.5 or greater and about 7.4 or less, about 4.5 or greater and about 7.3 or less, about 4.5 or greater and about 7.2 or less, about 4.5 or greater and about 7.1 or less, about 4.5 or greater and about 7.0 or less, about 4.5 or greater and about 6.9 or less, about 4.5 or greater and about 6.8 or less, about 4.5 or greater and about 6.7 or less, about 4.5 or greater and about 6.6 or less, about 4.5 or greater and about 6.5 or less, about 4.5 or greater and about 6.4 or less, about 4.5 or greater and about 6.3 or less, about 4.5 or greater and about 6.2 or less, about 4.5 or greater and about 6.1 or less, about 4.5 or greater and about 6.0 or less, about 4.5 or greater and about 5.9 or less, about 4.5 or greater and about 5.8 or less, about 4.5 or greater and about 5.7 or less, about 4.5 or greater and about 5.6 or less, about 4.5 or greater and about 5.5 or less, about 4.5 or greater and about 5.4 or less, about 4.5 or greater and about 5.3 or less, about 4.5 or greater and about 5.2 or less, about 4.5 or greater and about 5.1 or less, about 4.5 or greater and about 5.0 or less, about 4.5 or greater and about 4.9 or less, about 4.5 or greater and about 4.8 or less, about 4.5 or greater and about 4.7 or less, or about 4.5 or greater and about 4.6 or less, i.e., a neutralization agent with an acid dissociation constant in the range of about 4.5 or greater and about 7.5 or less, about 4.6 or greater and about 7.5 or less, about 4.7 or greater and about 7.5 or less, about 4.8 or greater and about 7.5 or less, about 4.9 or greater and about 7.5 or less, about 5.0 or greater and about 7.5 or less, about 5.1 or greater and about 7.5 or less, about 5.2 or greater and about 7.5 or less, about 5.3 or greater and about 7.5 or less, about 5.4 or greater and about 7.5 or less, about 5.5 or greater and about 7.5 or less, about 5.6 or greater and about 7.5 or less, about 5.7 or greater and about 7.5 or less, about 5.8 or greater and about 7.5 or less, about 5.9 or greater and about 7.5 or less, about 6.0 or greater and about 7.5 or less, about 6.1 or greater and about 7.5 or less, about 6.2 or greater and about 7.5 or less, about 6.3 or greater and about 7.5 or less, about 6.4 or greater and about 7.5 or less, about 6.5 or greater and about 7.5 or less, about 6.6 or greater and about 7.5 or less, about 6.7 or greater and about 7.5 or less, about 6.8 or greater and about 7.5 or less, about 6.9 or greater and about 7.5 or less, about 7.0 or greater and about 7.5 or less, about 7.1 or greater and about 7.5 or less, about 7.2 or greater and about 7.5 or less, about 7.3 or greater and about 7.5 or less, about 7.4 or greater and about 7.5 or less, about 4.5 or greater and about 7.4 or less, about 4.5 or greater and about 7.3 or less, about 4.5 or greater and about 7.2 or less, about 4.5 or greater and about 7.1 or less, about 4.5 or greater and about 7.0 or less, about 4.5 or greater and about 6.9 or less, about 4.5 or greater and about 6.8 or less, about 4.5 or greater and about 6.7 or less, about 4.5 or greater and about 6.6 or less, about 4.5 or greater and about 6.5 or less, about 4.5 or greater and about 6.4 or less, about 4.5 or greater and about 6.3 or less, about 4.5 or greater and about 6.2 or less, about 4.5 or greater and about 6.1 or less, about 4.5 or greater and about 6.0 or less, about 4.5 or greater and about 5.9 or less, about 4.5 or greater and about 5.8 or less, about 4.5 or greater and about 5.7 or less, about 4.5 or greater and about 5.6 or less, about 4.5 or greater and about 5.5 or less, about 4.5 or greater and about 5.4 or less, about 4.5 or greater and about 5.3 or less, about 4.5 or greater and about 5.2 or less, about 4.5 or greater and about 5.1 or less, about 4.5 or greater and about 5.0 or less, about 4.5 or greater and about 4.9 or less, about 4.5 or greater and about 4.8 or less, about 4.5 or greater and about 4.7 or less, or about 4.5 or greater and about 4.6 or less is desirable.

The conditions for a neutralization agent are basically in accordance with the content of PCT/JP2014/006379, but the pH is 6.0 or greater. If possible, pH of 6.0 or greater and 11.0 or less is desirable, and pH of 10.3 to 10.7 is optimal. TAL is desirably 20 or greater and optimally 2000. More importantly than these conditions, the neutralization agent must have high buffering power in the pH range of 4.5 or greater to 7.5.

Although not wishing to be bound by any theory, the neutralization agent can use an inorganic acid, an inorganic acid salt, an organic acid, an organic acid salt, a hydroxide salt or the like, but compliance with the above conditions is prioritized above all.

This is because adsorbed chlorine dioxide gas and chlorous acid could all become sodium chlorite if a neutralization agent with a pH greater than those designated in PCT/JP2014/006379 is used, which needs to be prevented. For this reason, it is necessary to be aware that if an unsuitable neutralization agent is used, the significance of using the manufacturing method with the features according to the present invention could disappear. This is not applicable if chlorine dioxide gas and chlorous acid can be prevented from completely becoming sodium chlorite.

Since an aqueous solution including a chlorate obtained by electrolysis contains a byproduct hypochlorite in some cases, an acid prepared by adding thiosulfate to sulfuric acid is slowly added. At this time, hypochlorite reacts with sulfuric acid, resulting in chlorine gas (formula I). Meanwhile, acidic thiosulfuric acid desalted in an acidic state converts some of chlorate to chlorous acid (formula J) and is simultaneously gasified, so that this is trapped in a neutralization solution.

$$2NaClO+H_2SO_4 \rightarrow Cl_2+Na_2SO_4+O_2 \quad \text{(formula I)}$$

$$H_2S_2O_3+4HClO_3+H_2O \rightarrow 4HClO_2+2H_2SO_4 \quad \text{(formula J)}$$

It is most desirable to use sulfuric acid as the acid, but phosphoric acid or nitric acid may be used.

The acid and acidic thiosulfuric acid are suitably mixed at an amount of about 0% (w/v) to about 1.3% (w/v) with respect to about 70% (w/w) aqueous solution of acid to be added. The optimal concentration of acidic thiosulfuric acid is desirably about 0.5% to about 0.7%.

Once it is confirmed that addition of sulfuric acid mixed with thiosulfate results in no more violent reactions and bubbles and no generation of the first reaction gas, hydrogen peroxide mixed with acidic thiosulfuric acid or dithionous acid is slowly added. At this time, the second reaction gas (formula C, J, or K) is generated, so that this is trapped in a neutralization solution.

$$H_2S_2O_4+3HClO_3+H_2O \rightarrow 3HClO_2+2H_2SO_4 \quad \text{(formula K)}$$

Other than acidic thiosulfuric acid or dithionous acid, peroxymonosulfuric acid, peroxydisulfuric acid, peroxyphosphoric acid, peroxychromic acid, or manganese oxide may be used.

35% hydrogen peroxide is used, to which acidic thiosulfuric acid or dithionous acid is mixed at about 0% to about 1.5%. About 0.5% to about 1.0% or thereabout is desirable. A second reaction is started by adding this mixture to the reaction solution so that it is about 3 to about 5% (w/w) with respect to the entire blended amount.

Two types of gas including chlorous acid generated in a two stage reaction (first reaction gas and second reaction gas) are trapped in a neutralization agent.

An aqueous solution obtained with the neutralization agent is a chlorous acid aqueous solution.

If, in doing so, more of the first reaction gas is adsorbed, a chlorous acid aqueous solution with high reactivity can be obtained. If the second reaction gas is mainly adsorbed, a chlorous acid aqueous solution with a conventional characteristic obtained by a manufacturing method such as those in Patent Literature 1 can be obtained.

A single chlorous acid aqueous solution can be prepared by mixing solutions with first reaction gas and second reaction gas adsorbed to separate neutralization agents.

Neutralization agents may have the same components. Neutralization agents with different components may be also used if the above conditions are met.

Meanwhile, generated chlorous acid ($HClO_2$) has properties of decomposing early into chlorine dioxide gas or chlorine gas due to the presence of chloride ions (Cl—) or hypochlorous acid (HClO) and other reduced products, or multiple chlorous acid molecules inducing decomposition reactions on each other. For this reason, it is necessary to prepare chlorous acid so that the state of chlorous acid ($HClO_2$) can be maintained over a long period of time in order to be useful as an antimicrobial agent, sterilizing agent, microbe-removing agent, disinfecting agent, and antiviral agent.

A preferred embodiment includes the step of adding a buffer to the aqueous solution including a chlorous acid that has been manufactured, in order to maintain a cyclic reaction. Any one of an inorganic acid, an inorganic acid salt, an organic acid, and an organic acid salt, or two or more types thereof are mixed in. This is because addition of an extra step in this manner adjusts the pH or the like, creates a transitional state, and delay the decomposition reaction, so that chlorous acid ($HClO_2$) can be stably maintained over a long period of time.

A more preferred embodiment includes the step of mixing any one of an inorganic acid and an inorganic acid salt, or two or more types thereof, into the aqueous solution including the chlorous acid, in order to maintain a cyclic reaction. This is because addition of an extra step in this manner can adjust the pH or the like and adjust the transitional state.

A still more preferred embodiment includes the step of mixing any one of an inorganic acid and an inorganic acid salt, or two or more types thereof, into the aqueous solution including the chlorous acid, and then mixing any one of an inorganic acid, an inorganic acid salt, an organic acid, and an organic acid salt or two or more types thereof, in order to maintain a cyclic reaction. This is because addition of an extra step in this manner can adjust the pH or the like and adjust the transitional state.

In another embodiment, carbonic acid, phosphoric acid, boric acid, or sulfuric acid can be used as the inorganic acid in the above method, but phosphoric acid is preferred. Although not wishing to be bound by any theory, it is demonstrated that a chlorous acid aqueous solution can maintain a high buffering effect within a suitable pH range in a state of chlorous acid while retaining the antimicrobial effect, sterilizing effect, microbe-removing effect, disinfecting effect, and antiviral effect by using phosphoric acid in particular in the present invention.

In another embodiment, carbonate, hydroxide salt, phosphate, or borate can be used as the inorganic acid, but phosphate is preferred. Hydroxide salt is encompassed in the scope of inorganic acid salts herein. Although not wishing to be bound by any theory, it is demonstrated that a chlorous acid aqueous solution can maintain high buffering effect within a suitable pH range in a state of chlorous acid while retaining the antimicrobial effect, sterilizing effect, microbe-removing effect, disinfecting effect, and antiviral effect by using phosphate in particular in the present invention.

In another embodiment, sodium carbonate, potassium carbonate, sodium bicarbonate, or potassium bicarbonate can be used as carbonate. Preferably, sodium carbonate can be used. This is because it has buffering power at two pH regions of weak alkaline region and weak acidic region, so that chlorous acid can be more advantageously stabilized in these regions.

In still another embodiment, examples of hydroxide salts include inorganic hydroxides. For example, sodium hydroxide or potassium hydroxide, calcium hydroxide, or barium hydroxide can be used. Sodium hydroxide or potassium hydroxide is preferred. Although not wishing to be bound by any theory, such hydroxide salts can be used to increase chlorous acid content. Meanwhile, use of a divalent salt can be advantageous because desalting is possible in combined use with phosphoric acid such that the amount of salt to chlorous acid and chlorite ions can be reduced.

In a preferred embodiment, sodium hydroxide or potassium hydroxide is 0.1 N to 1.0 N, and buffer pH of sodium phosphate and potassium phosphate is 5.0 to 7.5, especially pH of 5.0 to 7.0. This is because the effect thereof is unexpectedly enhanced stably for a long period of time, more than the previously-expected levels, with such constitution and pH.

In another embodiment, disodium hydrogen phosphate, sodium dihydrogen phosphate, trisodium phosphate, tripotassium phosphate, dipotassium hydrogen phosphate, or potassium dihydrogen phosphate can be used as the phosphate. Although not wishing to be bound by any theory, this is because these phosphates can have buffering power in a useful pH region exerting the most antimicrobial power, sterilizing power, microbe-removing power, disinfecting power, and antiviral power, which is a pH from 5 to 6. This can be advantageous because chlorous acid can be stable in this pH region. Furthermore, although not wishing to be bound by any theory, the present invention demonstrates that a longer and more stable transitional state can be created and chlorous acid ($HClO_2$) can be maintained over a longer period of time by delaying a decomposition reaction when using potassium salt (potassium hydroxide, potassium phosphate salt (e.g., tripotassium phosphate, dipotassium hydrogen phosphate, or potassium dihydrogen phosphate)) as metal, in comparison to cases using sodium salt (e.g., sodium hydroxide, sodium phosphate salt (disodium hydrogen phosphate, sodium dihydrogen phosphate, trisodium phosphate) as metal. Preferably, dipotassium hydrogen phosphate can be used.

In another embodiment, sodium borate or potassium borate can be used as borate. A potassium salt is preferred, but borate is not limited thereto.

In yet another embodiment, succinic acid, citric acid, malic acid, acetic acid, or lactic acid can be used as an organic acid. Succinic acid can be preferably used. Although not wishing to be bound by any theory, succinic acid can have buffering power from a pH of 5 level to 4 level. Drastic gasification of chlorine dioxide can be suppressed within this range of pH. However, pH tends to drastically decrease when pH is less than 5 level, in which case use of organic acid with a buffering power at a pH from 3 level such as citric acid is desirable.

In yet another embodiment, sodium succinate, potassium succinate, sodium citrate, potassium citrate, sodium malate, potassium malate, sodium acetate, potassium acetate, sodium lactate, potassium lactate, or calcium lactate can be used as an organic acid salt.

When an acid and/or a salt thereof is added, a transitional state, such as $Na^+ + ClO_2^- <-> Na-ClO_2$, $K^+ + ClO_2^- <-> K-ClO_2$, or $H^+ + ClO_2^- <-> H-ClO_2$ can be temporarily created to delay the progression of chlorous acid ($HClO_2$) to chlorine dioxide ($ClO_2$), which enables the manufacture of an aqueous solution including chlorous acid ($HClO_2$) that maintains chlorous acid for a long period of time and generates little chlorine dioxide ($ClO_2$). Although not wishing to be bound by any theory, it was demonstrated in the present invention that such an effect of maintaining is enhanced by using a phosphoric acid buffering agent. Although not wishing to be bound by any theory, it was further demonstrated in the present invention that such an effect of maintaining is further enhanced by using potassium salt relative to a case of using sodium salt or the like.

The following represents the decomposition of chlorite in an acidic solution in chemical formula 2.

[Chemical 3]

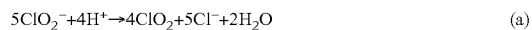

$5ClO_2^- + 4H^+ \rightarrow 4ClO_2 + 5Cl^- + 2H_2O$     (a)

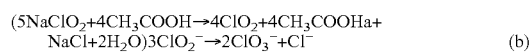

$(5NaClO_2 + 4CH_3COOH \rightarrow 4ClO_2 + 4CH_3COONa + NaCl + 2H_2O) 3ClO_2^- \rightarrow 2ClO_3^- + Cl^-$     (b)

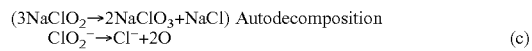

$(3NaClO_2 \rightarrow 2NaClO_3 + NaCl)$ Autodecomposition
$ClO_2^- \rightarrow Cl^- + 2O$     (c)

As represented in the formula, the rate of decomposition of an aqueous sodium chlorite solution in terms of pH is higher when pH is lower, i.e., when acidity is stronger. That is, the absolute rates of reactions (a), (b), and (c) in the above formula increase. For example, although the ratio accounted for by reaction (a) decreases for a lower pH, the total decomposition rate changes significantly, i.e., increases. Thus, the amount of generated chlorine dioxide ($ClO_2$) increases with the decrease in pH. Thus, the lower pH value results in earlier bleaching as well as antimicrobial power, sterilizing power, microbe-removing power, disinfecting power, and antiviral power. However, stimulatory and harmful chlorine dioxide gas ($ClO_2$) renders an operation difficult and negatively affects the health of a human being. Further, a reaction from chlorous acid to chlorine dioxide progresses quickly, resulting in the chlorous acid becoming unstable. In addition, the time an antimicrobial power, sterilizing power, microbe-removing power, disinfecting power, and antiviral power is maintained is very short.

In this regard, when the inorganic acid, inorganic acid salt, organic acid or organic acid salt is added to an aqueous solution including chlorous acid ($HClO_2$), pH values are adjusted within the range of 3.2 to 8.5, or within a preferred range such as pH 3.2 to 7.0 or pH 5.0 to 7.0 in accordance with the objective, from the viewpoint of balancing suppression of chlorine dioxide generation and sterilizing power.

When a spectrometric measurement of a sample can simultaneously identify an absorbent section including an acidic chlorite ion ($H^+ + ClO_2^-$) representing a peak near 260 nm and an absorbent section including chlorine dioxide ($ClO_2$) representing a peak near 350 nm between wavelengths of about 240 to about 420 nm, it is possible to recognize the presence of the chlorous acid aqueous solution of the present invention, i.e., the presence of chlorous acid ($HClO_2$). This is because a cyclic reaction involving the main constituent chlorous acid ($HClO_2$), chlorine dioxide ($ClO_2$), and acidic chlorite ion ($H^+ + ClO_2^-$) is simultaneously in progress as shown in the following Chemical Formula 4.

[Chemical 4]

Cyclic reaction of chlorous acid, chlorine dioxide, and acidic chlorite ion.

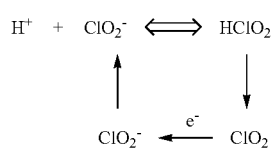

Conversion of chlorous acid ($HClO_2$) to chlorine dioxide ($ClO_2$) results in a single peak only near 350 nm.

It has already been found that pH can be further stabilized at this time by directly adding a buffering agent or by first adjusting the pH with sodium carbonate or the like and then adding another buffering agent.

Although not wishing to be bound by any theory, it was discovered that the present invention unexpectedly maintains an antimicrobial effect, sterilizing effect, microbe-removing effect, disinfecting effect, and antiviral effect while achieving the effect stably for a long period of time because a combination of chlorous acid ($HClO_2$), chlorine dioxide gas ($ClO_2$), or an aqueous solution including the same and any one of an inorganic acid, inorganic acid salt, organic acid, and organic acid salt, two or more types thereof, or a combination thereof can create a transitional state and delay a decomposition reaction to stabilize and maintain chlorous acid ($HClO_2$) over a long period of time. Examples of preferable ranges of pH include, but are not limited to, 3.2 or higher to less than 7.0, about 5.0 to about 7.5, about 5.0 to about 7.0, about 5.5 to about 7.0, about 5.0 to about 6.0, and the like. Examples of the lower limit include, but are not limited to, about 5.0, about 5.1, about 5.2, about 5.3, about 5.4, about 5.5, and the like, and examples of the upper limit include, but are not limited to, about 7.5, about 7.4, about 7.3, about 7.2, about 7.1, about 7.0, about 6.9, about 6.8, about 6.7, about 6.5, about 6.4, about 6.3, about 6.2, about 6.1, about 6.0, about 5.9, about 5.8, about 5.7, about 5.6, about 5.5, and the like. The optimal pH includes, but is not limited to, about 5.5. When "about" is used for a pH value herein, the range is intended to span 0.05 in both directions when the significant digit is the first decimal point. For example, about 5.5 is understood as referring to 5.45 to 5.55. For the purpose of distinction from sodium chlorite, pH is preferably, but not limited to, less than 7.0 in the present invention.

Preferable metal hydroxide includes sodium hydroxide and/or potassium hydroxide. Preferable metal phosphate includes sodium phosphate (e.g., disodium hydrogen phosphate, sodium dihydrogen phosphate, trisodium phosphate) and/or potassium phosphate (e.g., tripotassium phosphate, dipotassium hydrogen phosphate, and potassium dihydrogen phosphate; especially potassium dihydrogen phosphate), and still preferably potassium hydroxide and potassium phosphate (e.g., tripotassium phosphate, dipotassium hydrogen phosphate, and potassium dihydrogen phosphate; especially potassium dihydrogen phosphate), where the above are non-limiting examples.

In one aspect, the present invention provides an apparatus for manufacturing a chlorous acid aqueous solution, including: 1) an electrolytic cell for electrolyzing a salt to obtain a chlorate or an aqueous solution thereof, and 2) a reaction tank for reducing the chlorate or an aqueous solution thereof to obtain an aqueous solution including a chlorous acid.

In one aspect, the present invention provides articles impregnated with the antimicrobial agent, sterilizing agent, microbe-removing agent, disinfecting agent, or antiviral agent of the present invention. An article that can be used as the article of the present invention is any article that can be impregnated with a chlorous acid aqueous solution to be used for antimicrobial, sterilizing, microbe-removing, disinfecting, and antiviral purposes and the like, including medical devices and the like. Examples thereof include, but are not limited to, a sheet, film, patch, brush, nonwoven fabric, paper, fabric, absorbent cotton, sponge, and the like.

(General Manufacturing Example of Chlorous Acid Aqueous Solution by Electrolysis)

Salt is added to a salt dissolving tank containing tap water until salt no longer dissolves to obtain a salt solution. The salt solution is transferred to fill an electrolytic cell and a storage tank. At this time, the solution is filtered to remove salt that has not dissolved. A hydrochloric acid diluent with a concentration of about 0.3% is placed in a hydrochloric acid titration apparatus to start titration. The pH value is adjusted while circulating the salt solution. A cooling apparatus is started up to circulate cooling water. A control panel is operated to generate electricity for conducting electricity through a rectifier. The solution after electrical conduction is transferred to a reaction tank. A neutralization tank is loaded with a neutralization solution and a gas washing apparatus is loaded with a gas washing solution in advance, and then a stirring apparatus of the reaction tank is started up, and an acid solution is slowly added to the solution after electrical conduction therein. At this time, the remaining acid solution is added after confirming that first reaction gas is not generated in the reaction tank. Furthermore, a hydrogen peroxide solution is slowly added to slowly generate second reaction gas, thus allowing the gas to adsorb to the neutralization solution in the neutralization tank. This operation is repeated as much as needed. The manufacture is completed when the specification is met.

Reference documents cited herein, such as a scientific article, patent or patent application, are incorporated herein by reference in the same manner as the entire content thereof is specifically described.

The present invention has been described while presenting preferred embodiments to facilitate understanding. Hereinafter, the present invention is described based on the Examples. However, the aforementioned description and the following Examples are provided solely for exemplification, not for limiting the present invention. Thus, the scope of the present invention is not limited to the Embodiments or Examples that are specifically described herein. The scope of the present invention is limited solely by the scope of the claims.

EXAMPLES

The present invention is described in more detail with the following Examples/Comparative Examples, but the interpretation of the present invention is not limited thereto. In addition, Examples obtained by appropriately combining the technical means disclosed in each Example are encompassed within the scope of the present invention.

When necessary, animals used in the following Examples were handled in compliance with the Declaration of Helsinki. For reagents, the specific products described in the Examples were used. However, the reagents can be substituted with an equivalent product from another manufacturer (Sigma, Wako Pure Chemical, Nacalai Tesque, or the like). There are cases herein where an abbreviation "CAAS" is used for a chlorous acid aqueous solution, but they are synonymous.

(Method of Evaluating Chlorous Acid Aqueous Solution)

The primary active ingredient of chlorous acid aqueous solutions is chlorous acid. Meanwhile, chlorous acid is often misunderstood to be the same as chlorine dioxide or sodium chlorite. Of course, chlorous acid aqueous solution is also different from acidified sodium chlorite (ASC).

In this regard, the following measurement method is proposed to guarantee and manage the effect of chlorous acid aqueous solutions distinctly from such similar chlorine oxides.

(Chlorous Acid Concentration)

The chlorous acid concentration can be found by a known iodometry. The concentration is a value denoted by converting the total amount of chlorine contained in a chlorous acid aqueous solution as the chlorous acid concentration. While a patent is not sought for the method, the principle thereof is the following.

Oxidation capability of chlorous acid is utilized to free iodine from potassium iodide under the acidity of sulfuric acid.

$$HClO_2 + 2H_2SO_4 + 4KI \rightarrow HCl + 2K_2SO_4 + 2H_2O + 2I_2$$

Next, the freed iodine molecule is reduced with a sodium thiosulfate solution. Titration is ended when decolorized.

$$2I_2 + 4Na_2S_2O_3 \rightarrow 2Na_2S_4O_6 + 4NaI$$

Near the end of titration, starch is added as an indicator to obtain a blue color (iodine-starch reaction). Titration is ended when the blue color is lost. The concentration of chlorous acid is found from the amount of sodium thiosulfate solution required to reduce the free iodine molecule.

(Preparation of Reagent)

About 10 w/w % potassium iodide solution; about 180 g of water is added to about 20 g of potassium iodide.

The reagent is prepared at the time of use. The solution remaining from use during the day should be discarded and never be used the next day.

About 10 w/w % sulfuric acid; about 100 g of sulfuric acid is added to about 900 g of water.

*sulfuric acid should be slowly added along a glass rod. 1 w/w % starch solution; about 494.5 g of water is added to about 5.0 g of starch (soluble) and about 0.5 g of sodium azide. The mixture is heated with a microwave (or electric heater). The starch (soluble) is dissolved while stirring with a glass rod once in a while. When the solution is transparent, heating is discontinued. The solution is cooled and refrigerated.

About 0.1 mol/L sodium thiosulfate solution; 24.82 g of sodium thiosulfate pentahydrate is dissolved in water so that the solution is about 1000 mL.

Standardization 10 mL of about 1/60 mol/L potassium iodate is accurately measured out. 10 mL of about 10 w/w % potassium iodide solution and 10 mL of about 10 w/w % sulfuric acid are added. The mixture was left standing in the dark for about 10 minutes. About 0.1 mol/L sodium thiosulfate solution is titrated until the color of the solution is light yellow. About 1 mL of 1 w/w % starch solution is then added. About 0.1 mol/L sodium thiosulfate solution is titrated until the solution loses its color. The factor (f) of the 0.1 mol/L sodium thiosulfate solution is found by the following equation.

$$\text{Factor } (f) = 10/v$$

v; amount of 0.1 mol/L sodium thiosulfate solution titrated (mL)

1/60 mol/L potassium iodate solution; 1.783 g of potassium iodate heated and dried in advance for about 2 hours at about 120° C. is dissolved into water so that the solution is 500 mL.

(Operation Method)

(1) About 20 g of sample solution is placed in a 300 mL Erlenmeyer flask with a ground glass stopper. Water is added so that the solution is about 200 mL.

(2) About 10 mL of about 10 w/w % potassium iodide solution and about 10 mL of about 10 w/w % sulfuric acid are added and left standing in the dark for 15 minutes.

(3) About 0.1 mol/L sodium thiosulfate solution is added until the color of the solution is light yellow. About 1 mL of 1 w/w % starch solution is then added. About 0.1 mol/L sodium thiosulfate solution is added until the solution loses its color.

However, about 0.1 mol/L sodium thiosulfate solution is placed in a 100 mL glass beaker, Pasteur pipettes (large/small) are used to add the solution, and the added weight (g) is recorded.

$$(CAW) = (1.7115 \times 10^{-3} \times V \times f/w) \times 1000000 \times k$$

(CAW); concentration of chlorous acid (ppm)
V; titrated amount of 0.1 mol/L sodium thiosulfate solution (mL)
f; factor of 0.1 mol/L sodium thiosulfate solution
w; weight (g) of sample solution measured out in operation (1)
k; dilution factor
$1.7115 \times 10^{-3}$; weight (g) of chlorous acid corresponding to 1 mL of 0.1 mol/L sodium thiosulfate solution (Oxidation Capability; Sodium Hypochlorite Converted Concentration)

The amount of chlorine of sodium hypochlorite is denoted not only as the available chlorine concentration derived by iodometry, but also as the amount of activated chlorine involved in the sterilizing effect contained in sodium hypochlorite, i.e., oxidation capability is denoted as free chlorine. It is well known that the free chlorine and available chlorine concentration of sodium hypochlorite show the same value. However, for chlorous acid aqueous solutions, the amount of activated chlorine involved in an antimicrobial effect, sterilizing effect, microbe-removing effect, disinfecting effect, and antiviral effect contained therein does not match the value of chlorous acid concentration obtained by the above measurement method. In this regard, it is necessary to find the oxidation capability of a chlorous acid aqueous solution by the same approach as the free chlorine of sodium hypochlorite. This can be quantified by the following method.

Oxidation capability of chlorous acid aqueous solution: the basis and principle of measurement of sodium hypochlorite converted concentration are based on the description in "Regulation of Water Supply Act, Appended Table 3, Absorption spectroscopy" and Japanese Pharmacopoeia [General Tests, Processes and Apparatus] 2.24.

Oxidation capability of chlorous acid aqueous solution: sodium hypochlorite converted concentration is found by the following method.

1. Apparatus and Adjustment Method

A spectrophotometer is used as a measuring apparatus. After adjusting the apparatus in advance by the operation method appended to the spectrophotometer, wavelengths, transmittance and the like are checked with the premise that they comply with the test. For wavelengths, a wavelength calibration optical filter is used to measure transmittance near the wavelength of a reference value shown on the test certificate under test conditions in the test certificate appended to each filter. The wavelength at which the transmittance exhibits the minimal value is read out. However, when a test is conducted, deviation between the measured wavelength and the wavelength of the reference value is to be ±0.5 nm or less. Measurement is to be repeated three times. Each of the measured values is to be within a mean value ±0.2 nm or less. For transmittance or absorbance, a transmittance calibration optical filter is used to read out the transmittance at the wavelength of a reference value shown on the test certificate under test conditions in the test certificate appended to each filter. Further, when a test is conducted, deviation between the measured transmittance and the reference transmittance is to be within the upper limit value and the lower limit value of relative precision shown in the test certificate plus 1%. Measurement is repeated three times. It is confirmed that each measured value of absorbance (or measured value of transmittance converted to absorbance) is within mean value ±0.002 when absorbance is 0.500 or less, and each of the values is within mean value ±0.004 when absorbance exceeds 0.500. It is desirable to confirm that transmittance plots out a straight line by using multiple transmittance calibration optical filters with different transmittance at the same wavelength.

2. Operation Method

An apparatus adjusted in advance is used. A light source, detector, measurement mode of the apparatus, measured wavelength or range of measured wavelengths, spectrum width, wavelength scanning rate and the like are selected and determined. Next, the apparatus is activated and left standing for a certain period of time to confirm that the apparatus operates stably. Further, a shutter is placed on a sample optical path to block out light, and the indicated value of transmittance at the measured wavelength or range of measured wavelengths is adjusted to be 0%. Furthermore, the shutter is removed, and the indicated value of transmittance at the measured wavelength or range of measured wavelengths is adjusted to be 100% (or absorbance to 0%), and a cell containing a control solution or the like is placed on the optical path. The cell containing a control solution or the like is placed on a sample optical path and the control optical path, and the indicated value of transmittance is adjusted to 100% (or absorbance to 0%). A specified solution or a solvent used in the test is used as the control solution.

3. Method of Drawing Calibration Curves

<<DPD Method (Sankei Method)>>

1.0 g of N,N-diethyl-p-phenylenediamine sulfate is pulverized in a mortar, to which 24 g of anhydrous sodium sulfate is added and mixed homogeneously to the extent the crystal grain is not pulverized. The resultant mixture is used as an "indicator". Potassium dihydrogen phosphate is dissolved in ion exchange water (or distilled water) such that it is 1.6 M. The solution is used as a "potassium dihydrogen phosphate solution". Dipotassium hydrogen phosphate is dissolved in ion exchange water (or distilled water) such that it is 1.6 M. The solution is used as a "dipotassium hydrogenphosphate solution". A solution prepared by mixing the potassium dihydrogen phosphate solution and dipotassium hydrogen phosphate solution and adjusting with potassium dihydrogen phosphate solution or dipotassium hydrogen phosphate solution so that the pH is 6.5 by using a pH meter is used as a "phosphate buffer solution". Chlorine gas generated from dripping sulfuric acid (1+4) into sodium hypochlorite is allowed to be absorbed into purified water to prepare chlorine water, which is then used to adjust the free chlorine concentration to 100 ppm. The solution is used as a "reference solution". (At this time, it is necessary to confirm that the diluted solution is 100 ppm). The reference solution is accurately measured out, to which ion exchange water (or distilled water) is added to make a solution including 0.01 mL, 0.02 mL, 0.05 mL, or 0.10 mL in 1 mL. The solution is used as a "standard solution". Further, 9.5 mL of the standard solution is measured out, to which 0.5 mL of phosphate buffer solution is added and mixed homogeneously. 0.1 g of indicator is added thereto and mixed. A test is conducted by ultraviolet-visible spectrophotometry [The Japanese Pharmacopoeia [General Tests, Processes and Apparatus] 2.24]. Absorbance at wavelength of 510 nm is measured, 9.5 mL of ion exchange water (or distilled water) is measured, 0.5 mL of phosphate buffer solution is added, and mixed homogeneously. The resultant solution is used as a "blank solution". Next, the blank solution is tested by ultraviolet-visible spectrophotometry [The Japanese Pharmacopoeia [General Tests, Processes and Apparatus] 2.24], and the absorbance at wavelength 510 nm is measured. The above operation is repeated three times. A value obtained by subtracting the absorbance of the blank solution from the absorbance of the standard solution is used to calculate a mean value of absorbance at each concentration. The calculated values are used to create "calibration curves" within one hour after preparing the reference solution by plotting oxidation power (≈free chlorine concentration) on the horizontal (X) axis and absorbance on the vertical (Y) axis on a graph.

4. Measurement Method Using Calibration Curves

<<DPD Method (Sankei Method)>>: Oxidation Capability Utilizing Calibration Curves: Calculation Method for Free Chlorine Concentration (Sodium Hypochlorite Converted Concentration)

1.0 g of N,N-diethyl-p-phenylenediamine sulfate is pulverized in a mortar, to which 24 g of anhydrous sodium sulfate is added and mixed homogeneously to the extent the crystal grain is not pulverized. The resultant mixture is used as an "indicator". Potassium dihydrogen phosphate is dissolved in ion exchange water (or distilled water) such that it is 1.6 M. The solution is used as a "potassium dihydrogen phosphate solution". Dipotassium hydrogen phosphate is dissolved in ion exchange water (or distilled water) such that it is 1.6 M. The solution is used as a "dipotassium hydrogen phosphate solution". A solution prepared by mixing the potassium dihydrogen phosphate solution and dipotassium hydrogen phosphate solution and adjusting with the potassium dihydrogen phosphate solution or dipotassium hydrogen phosphate solution so that the pH is 6.5 by using a pH meter is used as a "phosphate buffer solution". A chlorous acid aqueous solution is then adjusted to 300 ppm as the chlorous acid concentration by using ion exchange water (or distilled water). The solution is used as a "test solution". 9.5 mL of the test solution is then measured out, to which 0.5 mL of phosphate buffer solution is added and mixed. 0.1 g of the indicator is then added and mixed. Absorbance at the wavelength of 510 nm was immediately measured using a spectrophotometer. The "sodium hypochlorite converted concentration" is found from the relational expression ($Y=aX$, a: coefficient) by using the calibration curves created with the <<DPD method>> for the measured absorbance value.

(Phenol Coefficient Method)

The precise antimicrobial effect, sterilizing effect, microbe-removing effect, disinfecting effect, and antiviral effect of a chlorous acid aqueous solution can be guaranteed only after a comparison and evaluation thereof with the antimicrobial effect, sterilizing effect, microbe-removing effect, disinfecting effect, and antiviral effect of phenol on *E. coli*. The following is the operation method thereof.

Required Reagents

Phenol, Normal Broth Medium, Desoxycholate Medium, Sodium Chloride, and Sterilized Water Requirement Instruments Kitchen timer, gas stove, pot, various test tubes and glass instruments, pipetter (10 ml), pipetter (1 ml), test tube (dry heat sterilized), gas burner, pipette tip (dry heat sterilized), platinum inoculation loop, cotton swab Preparation of Reagent 5% phenol solution: Phenol is dissolved with hot water of about 70° C. 25 mL is measured out and precisely diluted to 500 mL with water (40° C.). The specific gravity at 20° C. is confirmed to be within the range of 1.000±0.005.

Opacity does not Pose any Problems.

Liquid medium (1 L volume): 18.0 g of normal broth medium is added to 1 L of water in a 1000 mL Erlenmeyer flask with a stopper. They are mixed and dissolved for about 30 minutes at normal temperature. After confirming that the Operation Method

TABLE 1

| Blank segment | |
| --- | --- |
| Water | 9.0 |
| 5% phenol | 0.0 |
| Total | 9.0 |

*unit in mL

TABLE 2

| | Control segment | | | | | | | | | |
| --- | --- | --- | --- | --- | --- | --- | --- | --- | --- | --- |
| | Concentration setting % | | | | | | | | | |
| | 1.0 | 0.9 | 0.8 | 0.7 | 0.6 | 0.5 | 0.4 | 0.3 | 0.2 | 0.1 |
| Water | 7.0 | 7.2 | 7.4 | 7.6 | 7.8 | 8.0 | 8.2 | 8.4 | 8.6 | 8.8 |
| 5% phenol | 2.0 | 1.8 | 1.6 | 1.4 | 1.2 | 1.0 | 0.8 | 0.6 | 0.4 | 0.2 |
| Total | 9.0 | 9.0 | 9.0 | 9.0 | 9.0 | 9.0 | 9.0 | 9.0 | 9.0 | 9.0 |

*unit is mL medium has thoroughly dissolved, the solution is subjected to an autoclave (121° C., 15 minutes).

Liquid medium (volume of 200 mL): about 18.0 g of normal broth medium is added to 1 L of water. They were mixed and dissolved for about 30 minutes at normal temperature. After confirming that the medium has thoroughly dissolved, 200 mL of the solution is dispensed into a 300 mL Erlenmeyer flask with a stopper and subjected to an autoclave (121° C., 15 minutes).

Liquid medium (test tube): about 18.0 g of normal broth medium is added to 1 L of water. They were mixed and dissolved for about 30 minutes at normal temperature. After confirming that the medium has thoroughly dissolved, 10 mL of the solution is dispensed into each test tube, sealed with an aluminum cap, and subjected to an autoclave (121° C., 15 minutes).

Saline: About 8.5 g of sodium chloride is dissolved into about 500 ml of water. The solution is diluted with water to be 1 L and subjected to an autoclave (121° C., 15 minutes).

Microbial Solution (*E. coli*):

i) *E. coli* is smeared onto a newly created desoxycholate medium (flat plate) and cultured for about 24 hours at about 37° C.

ii) A single colony grown on the medium is suspended into 10 ml of saline. A liquid medium (volume of 200 mL) is inoculated with *E. coli* from a platinum inoculation loop, and the *E. coli* is cultured for about 24 hours at about 37° C.

iii) *E. coli* grows, rendering the liquid medium (test tube) opaque. The number of *E. coli* contained in the liquid at this time is about $10^8$.

(iv) The microbial solution prepared in iii) is used after diluting the solution 10-fold with saline and stirring the solution with a vortex mixer. The number of *E. coli* contained in the liquid at this time is about $10^7$.

Desoxycholate medium (flat plate): About 45 g of desoxycholate medium is added to 1 L of water, heated in an autoclave (105° C., 5 minutes), then cooled to about 50° C. About 20 mL of the medium is then seeded in a Petri dish and immobilized to prepare a plating medium.

Sterilized water: A suitable amount of distilled water is placed in a pharmaceutical glass bottle and subjected to an autoclave (121° C., 15 minutes).

Experiment Segment (e.g., Chlorous Acid Aqueous Solution)

Each sample is adjusted to have the following oxidation capability value. A required volume of each sample is prepared.

TABLE 3

| | Oxidation capability setting (DPD) | | | | | | | |
| --- | --- | --- | --- | --- | --- | --- | --- | --- |
| | 4 | 2 | 1.0 | 0.8 | 0.6 | 0.4 | 0.2 | 0.1 |
| Volume prior to adding microbial solution (mL) | 9.0 | 9.0 | 9.0 | 9.0 | 9.0 | 9.0 | 9.0 | 9.0 |

The prepared samples are dispensed into test tubes subjected to dry heat sterilization in accordance with the above formulation.

About 1 mL of microbial solution is added to each sample with 0 minute of contact. The number of *E. coli* contained in the microbial solution at this time is about 106.

After the microbial solution has been in contact with the sample, a sterilized platinum inoculation loop is immersed in the liquid medium after 5 minutes and 10 minutes. A water film is made in the ring at the tip of the platinum inoculation loop. The liquid medium (test tube) is inoculated in this state.

The inoculated test tube is placed in a vortex mixer and sealed, and incubated for 24 hours at 37° C. Test segments observed to have opacity after incubation are recorded as "+" and test segments without opacity are recorded as "−". However, a cotton swab is immersed in the liquid medium of the test segments evaluated as "+", and the medium is smeared onto a desoxycholate medium (flat plate) from the center to the outside so as to draw a straight line. The sample name is described on the back surface of the Petri dish where the medium was smeared, and the sample is cultured for 24 hours at 37° C.

After culturing for a predetermined time, samples observed to have a typical red colony where the medium was smeared are evaluated as "+", and samples with no observed red colony is evaluated as "−". The records are corrected accordingly. The evaluation for contact time of 5 minutes and contact time of 10 minutes is confirmed to be "+" "+" or "+" "−" or "−" "−". If "+" "−", the mean value of the range is found.

If there is no test segment with "+" "−", the intermediate value of the range where "+" "+" becomes "−" "−" is used.

The dilution factors of the value used are found from the stock solution of chlorous acid aqueous solution and stock solution of phenol as "dilution factor of sample solution" and "dilution factor of phenol", respectively, which are plugged into the following equations to find the phenol coefficient (PC).

TABLE 4

| Equation 1 | Dilution factor of sample solution = value of oxidation capability (TMB) of stock solution of chlorous acid aqueous solution/value of oxidation capability of chlorous acid aqueous solution used |
|---|---|
| Equation 2 | Dilution factor of phenol = 100/value of concentration of phenol used |
| Equation 3 | Phenol constant (PC) = dilution factor of sample solution/dilution factor of phenol |

TABLE 5

(Example) Control segment: phenol

| | Concentration settings % | | | | | | | | | |
|---|---|---|---|---|---|---|---|---|---|---|
| | 1.0 | 0.9 | 0.8 | 0.7 | 0.6 | 0.5 | 0.4 | 0.3 | 0.2 | 0.1 |
| 5 minute contact | − | − | − | + | + | + | + | + | + | + |
| 10 minute contact | − | − | − | + | + | + | + | + | + | + |
| Dilution factor | 100 | 111 | 125 | 142 | 166 | 200 | 250 | 333 | 500 | 1000 |

In this case, the concentration setting used is determined to be 0.75%, and the dilution factor is 133.

For chlorous acid aqueous solutions, the phenol coefficient is evaluated as shown in the following result table.

TABLE 6

(Example) Chlorous acid aqueous solution (Oxidation capability □ □)

| | Oxidation capability setting (DPD) | | | | | | | |
|---|---|---|---|---|---|---|---|---|
| | 4 | 2 | 1.0 | 0.8 | 0.6 | 0.4 | 0.2 | 0.1 |
| 5 minute contact | − | − | − | − | − | − | + | + |
| 10 minute contact | − | − | − | − | − | + | + | + |
| Dilution factor | | | | | | □ □/0.4 | | |

(Indicator of Chlorous Acid Aqueous Solution)

It is known that an antimicrobial effect, sterilizing effect, microbe-removing effect, disinfecting effect, and antiviral effect of chlorine oxides have different antimicrobial effect, sterilizing effect, microbe-removing effect, disinfecting effect, and antiviral effect that can be exerted with respect to 1 oxidation capability depending on the type of main active ingredient. If this is quantified using "phenol coefficient per oxidation capability (100)", the antimicrobial effect, sterilizing effect, microbe-removing effect, disinfecting effect, and antiviral effect can be handled separately for chlorous acid contained in an chlorous acid aqueous solution, chlorine dioxide, sodium chlorite, and ASC.

Example 1: Difference in Relationship of Phenol Coefficient and Oxidation Capability of Chlorine Dioxide, Sodium Chlorite and Chlorous Acid Aqueous Solution The following samples were prepared to measure the oxidation capability: sodium hypochlorite converted concentration and phenol coefficient for each of the chlorine oxides.

TABLE 7

| Name of sample | Preparation method |
|---|---|
| Sodium chlorite | Reagent: Aqueous solution prepared by measuring out 31.25 g of sodium chlorite (80% product, Wako) and dissolving the sodium chlorite into 100 ml of ion exchange water, wherein maximum absorbance section of UV spectrum can be observed only at 260 nm. |
| Chlorous acid aqueous solution A | Chlorous acid aqueous solution manufactured according to the manufacturing method in Example 2, wherein maximum absorbance sections of UV spectrum can be observed at both 260 nm and 350 nm. |
| Chlorine dioxide | Reagent: Aqueous solution prepared by measuring out 31.25 g of sodium chlorite (80% product, Wako), dissolving the sodium chlorite into 100 ml of ion exchange water, diluting the solution to 1200 ppm, and adding 0.1 mol/L hydrochloric acid thereto so that the pH would be 2.3 or less, wherein maximum absorbance section of UV spectrum can be observed only near 350 nm. |
| Dissolved chlorine dioxide | Reagent: Aqueous solution prepared by measuring out 31.25 g of sodium chlorite (80% product, Wako), dissolving the sodium chlorite into 100 ml of ion exchange water, adding 0.1 mol/L hydrochloric acid thereto to generate chlorine dioxide gas, and dissolving the gas into ultrapure water, wherein the available chlorine concentration at this time is 0.3% (w/v) and the maximum absorbance section of UV spectrum can be observed only near 350 nm. |

These samples were used to measure the oxidation capability: sodium hypochlorite converted concentration and phenol coefficient while appropriately dilution with ion exchange water.

Figure 4:
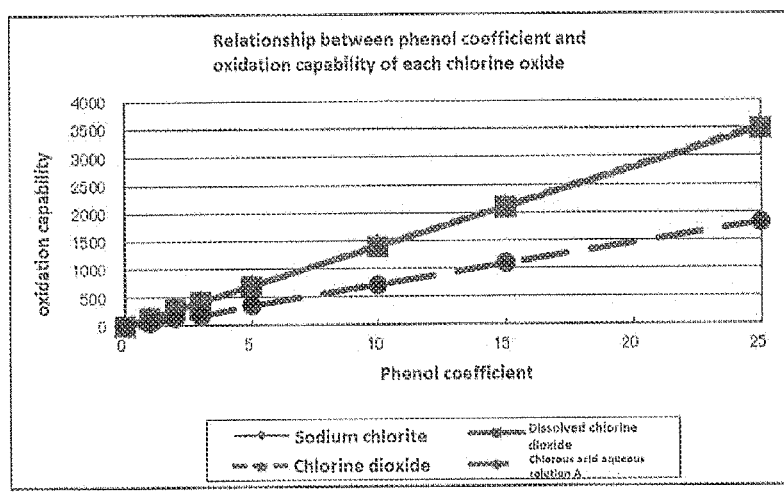
FIG. 4 is a graph showing the relationship between the phenol coefficient and oxidation capability for each chlorine oxide measured in Example 4. The vertical axis indicates the oxidation capability, and the horizontal axis indicates the phenol coefficient.

The results are shown below. This table and FIG. 4 describe the oxidation capability: sodium hypochlorite converted concentration at each phenol coefficient.

TABLE 8

| Phenol coefficient | Sodium chlorite | Dissolved chlorine dioxide | Chlorine dioxide | Chlorous acid aqueous solution A |
|---|---|---|---|---|
| 0 | 0 | 0 | 0 | 0 |
| 1 | nonexistent | 139 | 141 | 53 |
| 2 | nonexistent | 279 | 282 | 134 |
| 3 | nonexistent | 418 | 423 | 174 |
| 5 | nonexistent | 697 | 705 | 355 |
| 10 | nonexistent | 1395 | 1410 | 719 |
| 15 | nonexistent | 2092 | 2115 | 1092 |
| 25 | nonexistent | 3487 | 3525 | 1820 |

Sodium chlorite, despite having an available chlorine concentration of 25% (w/v) that corresponds to the saturation concentration, had oxidation capability and phenol coefficient of "0".

While the relationship between the oxidation capability and phenol coefficient of chlorine dioxide and dissolved chlorine dioxide matched, only chlorous acid aqueous solution A exhibited a high phenol coefficient with low oxidation capability, which is a tendency that is clearly different from the relationship between oxidation capability and phenol coefficient of sodium chlorite and chlorine dioxide. This demonstrates that the oxidation capability of chlorous acid aqueous solution A has a higher antimicrobial effect, sterilizing effect, microbe-removing effect, disinfecting effect, and antiviral effect than the oxidation capability of chlorine dioxide or sodium chlorite.

There are many experts who mistakenly consider and evaluate chlorous acid aqueous solution and ASC to be exactly the same due to having the same sterilizing component, chlorous acid. In this regard, ASC was prepared by faithfully reproducing WO 99/18805 by Kross to compare ASC with chlorous acid aqueous solution A manufactured in Example 2.

The following sample was prepared. The oxidation capability and phenol coefficient were measured immediately after manufacture and on day 5.

TABLE 9

| Name of sample | Preparation method |
|---|---|
| Chlorous acid aqueous solution A | Chlorous acid aqueous solution manufactured according to the manufacturing method in Example 2, wherein maximum absorbance sections of UV spectrum can be observed at both 260 nm and 350 nm. |
| ASC | ASC prepared by adding citric acid (claim 3) to an aqueous solution of chlorite with an available chlorine concentration of 1200 ppm (claim 2) so that the pH is 2.2 (claim 1) based on WO 99/18805 (available chlorine concentration 1200 ppm, pH 2.2) |

They were compared based on dissolved chlorine dioxide as the control.

TABLE 10

| Phenol coefficient | Chlorous acid aqueous solution A (D + 0) | Chlorous acid aqueous solution A (D + 5) | ASC (D + 0) | ASC (D + 5) | Dissolved chlorine dioxide |
|---|---|---|---|---|---|
| 0 | 0 | 0 | 0 | 0 | 0 |
| 1 | 53 | 39 | 85 | 131 | 139 |
| 2 | 134 | 152 | 186 | 302 | 279 |
| 3 | 174 | 178 | 284 | 422 | 418 |
| 5 | 355 | 345 | 474 | 703 | 697 |
| 10 | 719 | 760 | 948 | 1385 | 1395 |
| 15 | 1092 | 1140 | 1421 | 2078 | 2092 |
| 25 | 1820 | 1890 | 2369 | 3463 | 3487 |

Figure 5:
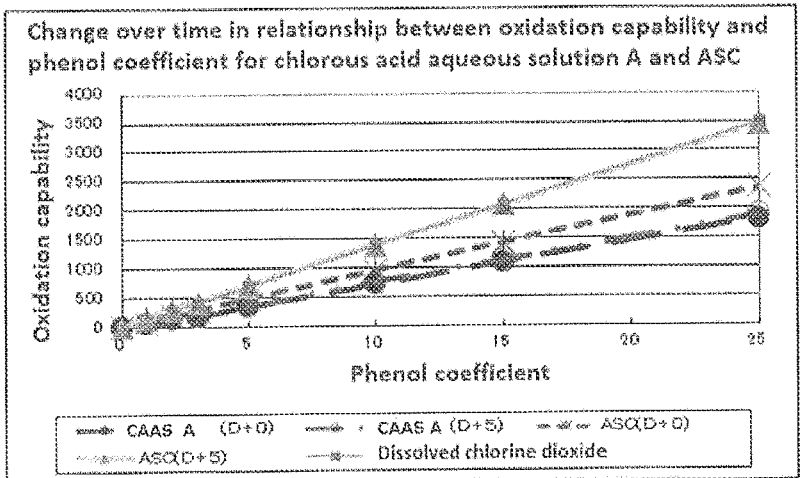
FIG. 5 is a graph showing the chronological change in the phenol coefficient and oxidation capability for chlorous acid aqueous solution A and ASC measured in Example 4. The vertical axis indicates the oxidation capability, and the horizontal axis indicates the phenol coefficient.

The relationship between oxidation capability and phenol coefficient did not change even after day 5 for chlorous acid aqueous solution A. Meanwhile, ASC exhibited a relationship between oxidation capability and phenol coefficient close to that of the chlorous acid aqueous solution immediately after preparation, but it was found that after 5 days, the oxidation capability and phenol coefficient were complete matches with those of the control, dissolved chlorine dioxide. It was found in view of the above that ASC is an antimicrobial agent, sterilizing agent, microbe-removing agent, disinfecting agent, or antiviral agent with properties that are closer to chlorine dioxide than chlorous acid aqueous solutions. (FIG. 5)

When the phenol coefficients of dissolved chlorine dioxide and chlorine dioxide were divided by the oxidation capability and multiplied by the ratio 100 (phenol coefficient per oxidation capability (100)) using the actual measurement values obtained in the above results, the value remained within a narrow range of 0.71 to 0.72. Further, the value of phenol coefficient per oxidation capability (100) of sodium chlorite was 0. Meanwhile, the phenol coefficient per oxidation capability (100) of chlorous acid aqueous solution A had a high value of about 1.37 to 1.87. Since the indicated range of values is wide, in a broad sense, a component can be determined not to be chlorine dioxide if the phenol coefficient per oxidation capability (100) is 0.72 or greater. With this indicator, it can be determined whether an antimicrobial component, sterilizing component, microbe-removing component, disinfecting component, or antiviral agent of a chlorine oxide is a chlorite ion, chlorous acid, or chlorine dioxide. It is desirable that the phenol coefficient per oxidation capability (100) of a chlorous acid aqueous solution is maintained at or above 1.0 if possible.

When a chlorous acid aqueous solution is used as an antimicrobial agent, sterilizing agent, microbe-removing agent, disinfecting agent, or antiviral agent, it is desirable to known the amount of activated chlorine involved in the antimicrobial effect, sterilizing effect, microbe-removing effect, disinfecting effect, or antiviral effect, i.e., how much oxidation capability is contained, with respect to the total chlorine content of the chlorous acid aqueous solution. This value can be managed with the value of oxidation capability per 100 ppm of chlorous acid concentration.

Furthermore, it is desirable to manage the value of phenol coefficient per 10000 ppm of chlorous acid concentration in order to manage the true antimicrobial effect, sterilizing effect, microbe-removing effect, disinfecting effect, and antiviral effect of chlorous acid contained in a chlorous acid aqueous solution.

For the antimicrobial effect, sterilizing effect, microbe-removing effect, disinfecting effect, and antiviral effect of chlorous acid aqueous solutions, the antimicrobial power, sterilizing power, microbe-removing power, disinfecting power, and antiviral power can be guaranteed, unlike sodium hypochlorite, by managing three values, i.e., "oxidation capability per 100 ppm of chlorous acid concentration", "phenol coefficient per oxidation capability (100)", and "phenol coefficient per 10000 ppm of chlorous acid concentration".

Example 2: Manufacture of Chlorous Acid Aqueous Solution with a Conventional Sterilizing Effect Function Manufactured in Patent Literature 1 in a Diaphragm Free Electrolytic Cell-Reaction Tank Integrated Manufacturing Plant (Example of Manufacturing Plant)

FIG. 1 shows an example of an integrated manufacturing plant that was used. In FIG. 1, each of the numbers is the member shown in the following Tables.

TABLE 11

| Number | Name |
| --- | --- |
| 1 | salt dissolving tank |
| 2 | saturated salt water filtration apparatus |
| 3 | pump 1 |
| 4 | control panel |
| 5 | rectifier/power source |
| 6 | electrolytic cell |
| 7 | storage tank |
| 8 | measurement instrument |
| 9 | pump 2 |
| 10 | cooling apparatus |
| 11 | hydrochloric acid titration apparatus |
| 12 | reaction tank |
| 13 | stirrer |
| 14 | acid adding apparatus |
| 15 | hydrogen peroxide adding apparatus |
| 16 | pump 3 |
| 17 | neutralization tank |
| 18 | gas washing tank |
| 19 | waste fluid treating tank |
| 20 | capacitor |
| 21 | jacket |

TABLE 12

| Number | Name |
| --- | --- |
| A | saturated salt water discharge valve |
| B | electrolytic cell discharge valve |
| C | air valve |
| D | circulation opening/closing spigot |
| E | liquor discharge valve |
| F | sulfuric acid inlet valve |
| G | hydrogen peroxide inlet valve |
| H | air pump spigot |
| I | trifurcated spigot |
| J | reaction solution discharge valve |
| K | air valve |
| L | sample valve |

The raw materials used and the formulation thereof that were used are the following.

TABLE 13

Formulation table a: Saturated salt water

| | Name of raw material | Amount |
| --- | --- | --- |
| 1 | Tap water | 65.0 g |
| 2 | Sodium chloride in the Japanese Pharmacopoeia | 35.0 g |
| Total | | 100 g |

TABLE 14

Formulation table b: Aqueous 0.1 mol/L hydrochloric acid solution (for titration)

| | Name of raw material | Amount |
| --- | --- | --- |
| 1 | Tap water | 65.0 g |
| 2 | Concentrated hydrochloric acid (98% product) | 35.0 g |
| Total | | 100 g |

TABLE 15

Formulation table c: Acid solution

| | Name of raw material | Amount |
| --- | --- | --- |
| 1 | Tap water | 300.0 g |
| 2 | Sulfuric acid | 700.0 g |
| Total | | 1000 g |

TABLE 16

Formulation table d: Hydrogen peroxide solution

| | Name of raw material | Amount |
| --- | --- | --- |
| 1 | Tap water | 64.0 g |
| 2 | Dithionous acid-sulfuric acid mixture | 1 g |
| 3 | Hydrogen peroxide (35% product) | 35.0 g |
| Total | | 100 g |

Dithionous acid-sulfuric acid mixture: 1 g of sodium dithionate is measured out and dissolved into 90 ml of ion exchange water, and the solution is adjusted to a pH of 2.0 or less with 0.05N sulfuric acid and diluted to 100 ml.

TABLE 17

Formulation table e: Reaction solution

| | Name of raw material | Amount |
| --- | --- | --- |
| 1 | Liquor | 200 g |
| 2 | Acid solution | 300 g |
| 3 | Hydrogen peroxide solution | 50 g |

TABLE 18

Formulation table f: Neutralization solution

| | Name of raw material | Amount |
| --- | --- | --- |
| 1 | Tap water | 731.88 g |
| 2 | Sodium hydroxide | 2.5 g |
| 3 | Dipotassium hydrogen phosphate | 139.36 g |
| 4 | Sodium carbonate | 53 g |
| 5 | Sodium tetraborate | 7.62 g |
| 6 | 35% hydrogen peroxide | 30 |
| | | 1000 g |

TABLE 19

Formulation table g: Gas washing solution

| | Name of raw material | Amount |
|---|---|---|
| 1 | Tap water | 910 g |
| 2 | Sodium hydroxide | 60 g |
| 3 | 35% hydrogen peroxide | 30 |
| Total | | 1000 g |

TABLE 20

Formulation table h: Waste fluid neutralization solution

| | Name of raw material | Amount |
|---|---|---|
| 1 | Tap water | 790.0 g |
| 2 | Sodium ascorbate | 150.0 g |
| 3 | Sodium hydroxide | 60 g |
| Total | | 1000 g |

(Summary of Manufacture of Chlorous Acid Aqueous Solution by Electrolysis)

Saturated salt water is prepared by adding salt that meets the specification of sodium chloride in the Japanese Pharmacopoeia to a salt dissolving tank containing tap water until the salt no longer dissolves. Pump 1 is started up to transfer the saturated salt water to fill an electrolytic cell and a storage tank. At this time, the saturated salt water is passed through a saturated salt water filtration apparatus to remove undissolved sodium chloride crystals. Hydrochloric acid diluent with a 0.3% concentration is placed in a hydrochloric acid titration apparatus to start titration. Pump 2 is started up to adjust the pH value to 6.0 while circulating the saturated salt water. pH and solution temperature monitors are started up to record the value at the time. A cooling apparatus is started up to circulate cooling water. A control panel is operated to generate electricity and start conducting electricity through a rectifier (voltage of 3V, current of 100 A, current density of 2500 A/m$^2$, 80° C.±5° C., and 78 hours and 30 minutes). The materials of electrodes connected to the electrolysis cell are platinum/iridium coated titanium (anode) and highly pure steel (cathode). These electrodes are disposed in parallel at a 5 mm interval without a diaphragm. The saturated salt water passes through this space to circulate the electrolytic cell and the storage tank. The concentration of sodium chlorate of liquid obtained at this time is 50% (w/v), and the available chlorine concentration was 0 ppm. Pump 2 is stopped, and the liquor is transferred to a reaction tank. A neutralization solution is loaded into a neutralization tank and a gas washing solution is loaded into a gas washing apparatus in advance, and then a stirring apparatus of the reaction tank is started up and an acid solution is slowly added to about 1 kg of the liquid in the reaction tank. At this time, the remaining acid solution is added after confirming that first reaction gas is not generated in the reaction tank. Furthermore, a hydrogen peroxide solution is slowly added to slowly generate second reaction gas. The gas is allowed to adsorb to the neutralization solution in the neutralization tank. This operation is repeated twice. The manufacture ends when the specification is met.

A chlorous acid aqueous solution was manufactured as described below.

(1. Preparation)

The following preparation was performed.
1. A was confirmed to be plugged.
2 Formulation table a was added to 1.
3 Formulation table b was added to 11.
4 B and D were opened, and E was confirmed to be plugged.
5 A was opened, and 3 was started up.
6 The solution of 1 was transferred until 6 and 7 were filled.
7 9 was started up to fill each pipe with the solution of 1.
8 A was plugged and 3 was stopped.
9 8 was started up to start measuring the pH and solution temperature.
10 11 was started up to adjust the pH of the flowing solution of 1 to 6.0.
11 10 was started up to allow cooling water to circulate to 21.
12 4 and 6 were started up to start conducting electricity.
13 4 and 5 were stopped.
14 L was opened for sampling.
15 L was closed.
16 The solution was circulated until the solution temperature was below 25° C.
17 Quality inspection was performed, and if the quality met the specification, 9 was stopped.
18 11 was stopped.
19 B and D were closed.
20 Formulation table c was added to 14.
21 Formulation table d was added to 15.
22 Formulation Table f was added to 17.
23 Formulation table g was added to 18
24 F, G, K, H, J, and I were confirmed to be closed.
25 C and K were opened.
26 E was opened to transfer the liquor of 7.
27 E was closed.
28 The amount of the transferred liquor was examined.
29 C and K were closed.
30 I was opened in the direction of 12→I→17.
31 13 was started up.
32 F was opened, and the syringe of 14 was pushed to slowly add Formulation table c to 12.
33 After confirming that first chlorous acid gas was not generated, all of Formulation table c was added to 12.
34 F was opened.
35 G was opened.
36 The syringe of 15 was pushed to slowly add Formulation table d to 12.
37 A violent reaction was induced, and when bubble generation has subsided, 16 was started up and H was opened.
38 The syringe of 15 was pushed to add all of the Formulation table d to 12.
39 G was closed.
40 After the completion of the reaction, H was closed and 16 was stopped.
41 13 was stopped.
42 I was opened in the direction of 19→I→17.
43 K was opened.
44 J was opened to transfer the solution to 19.
45 The operation from 25 to 44 was repeated twice.
46 Formulation table h was added to 19 to neutralize and discharge the solution.
47 18 was adjusted to normal pressure.
48 17 was adjusted to normal pressure, and the content of 17 was retrieved for quality inspection as chlorous acid aqueous solution A.

The results of the above quality inspection upon manufacture are described.

TABLE 21

| Manufacturing step | Measurement item | Actual measurement value | Amount transferred |
|---|---|---|---|
| Salt dissolving tank | Sodium chloride concentration | 33.77% | 2.2 kg |

TABLE 22

| Manufacturing step | Measurement item | | Actual measurement value | Measurement item | | Actual measurement value |
|---|---|---|---|---|---|---|
| Electrolytic cell | Before electric conduction | Solution temperature | 13.5° C. | After electric conduction | Solution temperature | 88.0° C. |
| | | pH | 6 | | pH | 6.5 |
| | Current | | 100 A | | | |
| | Voltage | | 3 V | | | |
| | Flow rate | | 0.2 kg/h | | | |
| | Uptime | | 78 hrs. and 30 min. | | | |
| Storage tank | Sodium chlorate concentration | | 52% | | | |
| | Available chlorine concentration | | 0 ppm | | | |

TABLE 23

| Reaction tank | | | First amount added | | Second amount added | |
|---|---|---|---|---|---|---|
| Liquor | | | 998 g | | 1010 g | |
| Acid | | | 1500 g | | 1500 g | |
| Hydrogen peroxide | | | 250 g | | 250 g | |
| Neutralization tank | Reaction No. | Reaction step | Chlorous acid concentration | Reaction No. | Reaction step | Chlorous acid concentration |
| | 1st | First reaction | 0 | 2nd | First reaction | Not measured |
| | | Second reaction | 25928 ppm | | Second reaction | 51926 ppm |
| | Amount of neutralization solution added | | 5 kg | Amount produced | | 5 kg |

Component analysis table for chlorous acid aqueous solution A

TABLE 24

Component analysis table for chlorous acid aqueous solution A

| Tested item | Specification | Result |
|---|---|---|
| Potassium permanganate | Addition of potassium permanganate solution (1 → 300) to 5 ml of the product (1 → 20) results in a purplish red color. Addition of 1 ml of sulfuric acid (1 → 20) thereto changes the color to light yellow. | Addition of potassium permanganate solution (1 → 300) to 5 ml of the product (1 → 20) resulted in a purplish red color. Addition of 1 ml of sulfuric acid (1 → 20) thereto changed the color to light yellow. |
| UV spectrum | An aqueous solution of the product has maximum absorbance sections at wavelengths of 258 to 262 nm and 346 to 361 nm. | An aqueous solution of the product had maximum absorbance sections at wavelengths of 258 to 262 nm and 346 to 361 nm. |
| Potassium iodide-starch paper | When potassium iodide-starch paper is immersed in the product, the paper changes its color to blue and then loses the color. | When potassium iodide-starch paper was immersed in the product, the paper changed its color to blue and then lost the color. |
| Chlorous acid concentration | — | 51926.48 ppm |

With the above chlorous acid aqueous solution A as the raw material, chlorous acid aqueous solution preparation A was prepared by adding the following formulation to maintain a cyclic reaction.

TABLE 25

Formulation table i: Formulation of chlorous acid aqueous solution preparation A

| | Name of raw material | Amount |
|---|---|---|
| 1 | Tap water | 789.04 g |
| 2 | Potassium dihydrogen phosphate | 54.43 g |
| 3 | Dipotassium hydrogen phosphate | 69.68 g |
| 4 | Chlorous acid aqueous solution A | 86.85 g |
| Total | | 1000 g |

TABLE 26

Component analysis table for chlorous acid aqueous solution preparation A

| Measured item | Specification value[1] | Actual measurement value |
|---|---|---|
| Chlorous acid concentration | 4500 ppm or greater | 4516 ppm |
| Oxidation capability | Not set | 152 |
| Phenol coefficient | Not set | 1.40 |
| Oxidation capability per 100 ppm of chlorous acid concentration | 1.1 or greater (self-imposed specification) | 3.36 |
| Phenol coefficient per oxidation capability (100) | 0.7 or greater (self-imposed specification) | 0.92 |
| Phenol coefficient per 10000 ppm of chlorous acid concentration | 1.5 or greater (self-imposed specification) | 3.10 |

[1]This can be any preferable value. The specification value does not necessarily need to be this value. This is a self-imposed specification of the Applicant.

Example 3: Manufacture of Highly Reactive Chlorous Acid Aqueous Solution by a Diaphragm Free Electrolytic Cell-Reaction Tank Integrated Manufacturing Plant The raw materials and the formulation thereof that were used are the following.

TABLE 27

Formulation table a: Saturated salt water

| | Name of raw material | Amount |
|---|---|---|
| 1 | Tap water | 65.0 g |
| 2 | Sodium chloride in the Japanese Pharmacopoeia | 35.0 g |
| Total | | 100 g |

TABLE 28

Formulation table b: Aqueous 0.1 mol/L hydrochloric acid solution (for titration)

| | Name of raw material | Amount |
|---|---|---|
| 1 | Tap water | 65.0 g |
| 2 | Concentrated hydrochloric acid (98% product) | 35.0 g |
| Total | | 100 g |

TABLE 29

Formulation table j: Acid solution

| | Name of raw material | Amount |
|---|---|---|
| 1 | Tap water | 295.0 g |
| 2 | Sodium thiosulfate | 5.0 g |
| 3 | Sulfuric acid | 700.0 g |
| Total | | 1000 g |

TABLE 30

Formulation table d: Hydrogen peroxide solution

| | Name of raw material | Amount |
|---|---|---|
| 1 | Tap water | 64.0 g |
| 2 | Dithionous acid-sulfuric acid mixture | 1 g |
| 3 | Hydrogen peroxide (35% product) | 35.0 g |
| Total | | 100 g |

Dithionous acid-sulfuric acid mixture: 1 g of sodium dithionate is measured out and dissolved into 90 ml of ion exchange water, and the solution is adjusted to a pH of 2.0 or less with 0.05N sulfuric acid and diluted to 100 ml.

TABLE 31

Formulation table e: Reaction solution

| | Name of raw material | Amount |
|---|---|---|
| 1 | Liquor | 200 g |
| 2 | Acid solution | 300 g |
| 3 | Hydrogen peroxide solution | 50 g |

TABLE 32

Formulation table f: Neutralization solution

| | Name of raw material | Amount |
|---|---|---|
| 1 | Tap water | 731.88 g |
| 2 | Sodium hydroxide | 2.5 g |
| 3 | Dipotassium hydrogen phosphate | 139.36 g |
| 4 | Sodium carbonate | 53 g |
| 5 | Sodium tetraborate | 7.62 g |
| 6 | 35% hydrogen peroxide | 30 |
| | | 1000 g |

TABLE 33

Formulation table g: Gas washing solution

| | Name of raw material | Amount |
|---|---|---|
| 1 | Tap water | 910 g |
| 2 | Sodium hydroxide | 60 g |
| 3 | 35% hydrogen peroxide | 30 |
| Total | | 1000 g |

TABLE 34

Formulation table h: Waste fluid neutralization solution

| | Name of raw material | Amount |
|---|---|---|
| 1 | Tap water | 790.0 g |
| 2 | Sodium ascorbate | 150.0 g |
| 3 | Sodium hydroxide | 60 g |
| Total | | 1000 g |

(Summary of Manufacture of Chlorous Acid Aqueous Solution by Electrolysis)

Saturated salt water is prepared by adding salt that meets the specification of sodium chloride in the Japanese Pharmacopoeia to a salt dissolving tank containing tap water until the salt no longer dissolves. Pump 1 is started up to transfer the saturated salt water to fill an electrolytic cell and a storage tank. At this time, the saturated salt water is passed through a saturated salt water filtration apparatus to remove undissolved sodium chloride crystals. Hydrochloric acid diluent with a 0.3% concentration is placed in a hydrochloric acid titration apparatus to start titration. Pump 2 is started up to adjust the pH value to 6.5 while circulating the saturated salt water. pH and solution temperature monitors are started up to record the value at the time. A cooling apparatus is started up to circulate cooling water. A control panel is operated to generate electricity and start conducting electricity through a rectifier (voltage of 3 V, current of 100 A, current density of 2500 A/m$^2$, 85° C.±5° C., and 78 hours and 30 minutes). The materials of electrodes connected to the electrolysis cell are platinum/iridium coated titanium (anode) and highly pure steel (cathode). These electrodes are disposed in parallel at a 5 mm interval without a diaphragm. The saturated salt water passes through this space to circulate the electrolytic cell and the storage tank. The concentration of sodium chlorate of liquid obtained at this time is 49% (w/v), and the available chlorine concentration was 9889 ppm. Pump 2 is stopped, and the liquor is transferred to a reaction tank. A neutralization solution is loaded into a neutralization tank and a gas washing solution is loaded into a gas washing apparatus in advance, and then a stirring apparatus of the reaction tank is started up and an acid solution is slowly added to about 1 kg of the liquid in the reaction tank. First reaction gas is allowed to be generated in the reaction tank and to adsorb to the neutralization solution in the neutralization tank. After adding the remaining acid solution and confirming that first reaction gas or bubbles is not generated, a hydrogen peroxide solution is slowly added to slowly generate second reaction gas. The gas is allowed to adsorb to the neutralization solution in the neutralization tank. This operation is repeated twice. The manufacture ends when the specification is met.

A chlorous acid aqueous solution was manufactured as described below.

(1. Preparation)

The following preparation was performed.
1. A was confirmed to be plugged.
2 Formulation table a was added to 1.
3 Formulation table b was added to 11.
4 B and D were opened, and E was confirmed to be plugged.
5 A was opened, and 3 was started up.
6 The solution of 1 was transferred until 6 and 7 were filled.
7 9 was started up to fill each pipe with the solution of 1.
8 A was plugged and 3 was stopped.
9 8 was started up to start measuring the pH and solution temperature.
10 11 was started up to adjust the pH of the flowing solution of 1 to 6.5.
11 10 was started up to allow cooling water to circulate to 21.
12 4 and 6 were started up to start conducting electricity.
13 4 and 5 were stopped.
14 L was opened for sampling.
15 L was closed.
16 The solution was circulated until the solution temperature was below 25° C.
17 Quality inspection was performed, and if the quality met the specification, 9 was stopped.
18 11 was stopped.
19 B and D were closed.
20 Formulation table j was added to 14.
21 Formulation table d was added to 15.
22 Formulation Table f was added to 17.
23 Formulation table g was added to 18.
24 F, G, K, H, J, and I were confirmed to be closed.
25 C and K were opened.
26 E was opened to transfer the liquor of 7.
27 E was closed.
28 The amount of the transferred liquor was examined.
29 C and K were closed.
30 I was opened in the direction of 12→I→17.
31 13 was started up.
32 F was opened, and the syringe of 14 was pushed to slowly add Formulation table j to 12.
33 Generated first reaction gas was allowed to absorb to Formulation table f at 17.
34 16 was started up and H was opened.
35 After confirming that first reaction gas is not generated, H was closed and 16 was stopped.
36 The syringe of 14 was pushed to add all of Formulation table j to 12.
37 F was opened.
38 G was opened.
39 The syringe of 15 was pushed to slowly add Formulation table d to 12.
40 A violent reaction was induced, and when bubble generation has subsided, 16 was started up and H was opened.
41 The syringe of 15 was pushed to add all of the Formulation table d to 12.
42 G was closed.
43 After the completion of the reaction, H was closed and 16 was stopped.
44 13 was stopped.
45 I was opened in the direction of 19→I→17.
46 K was opened.
47 J was opened to transfer the solution to 19.
48 The operation from 25 to 44 was repeated twice,
49 Formulation table h was added to 19 to neutralize and discharge the solution.
50 18 was adjusted to normal pressure.
51 17 was adjusted to normal pressure, and the content of 17 was retrieved for quality inspection as chlorous acid aqueous solution B.

The results of the above quality inspection upon manufacture are described.

TABLE 35

| Manufacturing step | Measurement item | Actual measurement value | Amount transferred |
|---|---|---|---|
| Salt dissolving tank | Sodium chloride concentration | 33.70% | 2.2 kg |

TABLE 36

| Manufacturing step | Measurement item | | Actual measurement value | Measurement item | | Actual measurement value |
|---|---|---|---|---|---|---|
| Electrolytic cell | Before electric conduction | Solution temperature | 13.5° C. | After electric conduction | Solution temperature | 80.0° C |
| | | pH | 6.5 | | pH | 7.2 |
| | Current | | 100 A | | | |
| | Voltage | | 3 V | | | |
| | Flow rate | | 0.2 kg/h | | | |
| | Uptime | | 78 hrs. and 30 min | | | |
| Storage tank | Sodium chlorate concentration | | 49% | | | |
| | Available chlorine concentration | | 9889 ppm | | | |

TABLE 37

| Reaction tank | First amount added | Second amount added |
|---|---|---|
| Liquor | 1010 g | 1013 g |
| Acid | 1500 g | 1500 g |
| Hydrogen peroxide | 250 g | 250 g |

| Neutralization tank | Reaction No. | Measurement item | Measurement value | Reaction No. | Measurement item | Measurement value |
|---|---|---|---|---|---|---|
| | 1st | Available chlorine concentration | 2325 ppm | 2nd | Available chlorine concentration | 4743 ppm |
| | | Chlorous acid aqueous solution concentration | 22855 ppm | | Chlorous acid aqueous solution concentration | 46999 ppm |
| | | Amount of neutralization solution added | 5 kg | | Amount produced | 5 kg |

Component analysis table for chlorous acid aqueous solution B

TABLE 38

| Tested item | Specification | Result |
|---|---|---|
| Potassium permanganate | Addition of potassium permanganate solution (1 → 300) to 5 ml of the product (1 → 20) results in a purplish red color. Addition of 1 ml of sulfuric acid (1 → 20) thereto changes the color to light yellow. | Addition of potassium permanganate solution (1 → 300) to 5 ml of the product (1 → 20) resulted in a purplish red color. Addition of 1 ml of sulfuric acid (1 → 20) thereto changed the color to light yellow. |
| UV spectrum | An aqueous solution of the product has maximum absorbance sections at wavelengths of 258 to 262 nm and 346 to 361 nm. | An aqueous solution of the product had maximum absorbance sections at wavelengths of 258 to 262 nm and 346 to 361 nm. |
| Potassium iodide-starch paper | When potassium iodide-starch paper is immersed in the product, the paper changes its color to blue and then loses the color. | When potassium iodide-starch paper was immersed in the product, the paper changed its color to blue and then lost the color. |
| Chlorous acid concentration | — | 46999.83 ppm |

With the above chlorous acid aqueous solution B as the raw material, chlorous acid aqueous solution preparation B was prepared by adding the following formulation to maintain a cyclic reaction.

TABLE 39

| Formulation table k: Formulation of chlorous acid aqueous solution preparation B | | |
|---|---|---|
| | Name of raw material | Amount |
| 1 | Tap water | 774.41 g |
| 2 | Potassium dihydrogen phosphate | 54.43 g |
| 3 | Dipotassium hydrogen phosphate | 69.68 g |
| 4 | Chlorous acid aqueous solution B | 101.48 g |
| Total | | 1000 g |

TABLE 40

Component analysis table for
chlorous acid aqueous solution preparation B

| Measured item | Specification value[1] | Actual measurement value |
|---|---|---|
| Chlorous acid concentration | 4500 ppm or greater | 4770 ppm |
| Oxidation capability | Not set | 572 |
| Phenol coefficient | Not set | 9.03 |
| Oxidation capability per 100 ppm of chlorous acid concentration | 1.1 or greater (self-imposed specification) | 11.99 |
| Phenol coefficient tper oxidation capability (100) | 0.7 or greater (self-imposed specification) | 1.57 |
| Phenol coefficient per 10000 ppm of chlorous acid concentration | 1.5 or greater (self-imposed specification) | 18.93 |

[1]This can be any preferable value. The specification value does not necessarily need to be this value. This is a self-imposed specification of the Applicant.

Example 4: Reactivity Investigation Test on Reactivity Retaining Chlorous Acid Aqueous Solution A comparative test was conducted for chlorous acid aqueous solution A manufactured in Example 2 and the preparation thereof, i.e., chlorous acid aqueous solution preparation A, as well as chlorous acid aqueous solution B manufactured in Example 3 and the preparation thereof, i.e., chlorous acid aqueous solution preparation B, in the absence of organic matters. A chlorous acid aqueous solution manufactured by the manufacturing method patent of Patent Literature 1 was used as the control.

The chlorous acid concentration, oxidation capability, and phenol coefficient of the chlorous acid aqueous solution of Patent Literature 1, chlorous acid aqueous solution A, chlorous acid aqueous solution preparation A, chlorous acid aqueous solution B, and chlorous acid aqueous solution preparation B were found. Furthermore, 1 ml of *E. coli* solution ($10^7$ *E. coli*) was added to 8 ml of saline and thoroughly stirred. 1 ml of the solution prepared by adjusting each of the chlorous acid aqueous solutions and chlorous acid aqueous solution preparations to the chlorous acid concentration of 200 ppm was added and contacted for 15 seconds, 30 seconds, 1 minute, 5 minutes, and 10 minutes. 0.1 N sodium thiosulfate as added to stop the reaction. 1 ml of the solution was placed on a broth plating medium and inoculated. The medium was cultured for 1 day at 35° C. This was performed immediately after manufacture, on day 10, and on day 30. The chlorous acid aqueous solutions and chlorous acid aqueous solution preparations were stored in the shade at a room temperature of 25° C.

The results immediately after manufacture are shown.

TABLE 41

| Name of sample | pH | Chlorous acid concentration | Oxidation capability | Phenol coefficient |
|---|---|---|---|---|
| Chlorous acid aqueous solution manufactured by the manufacturing method in Pat. Literature 1 | 6.09 | 30808 ppm | 1005 | 14.7 |
| Chlorous acid aqueous solution A | 6.16 | 51926 ppm | 1528 | 12.3 |
| Chlorous acid aqueous solution preparation A | 6.14 | 4516 ppm | 152 | 1.4 |
| Chlorous acid aqueous solution B | 6.52 | 46999 ppm | 5641 | 89.0 |
| Chlorous acid aqueous solution preparation B | 6.48 | 4770 ppm | 572 | 9.0 |

TABLE 42

| Name of sample | Chlorous acid concentration upon contact | Oxidation capability upon contact | Contact time to *E. coli* | | | | |
|---|---|---|---|---|---|---|---|
| | | | 15 sec | 30 sec | 1 min | 5 min | 10 min |
| Chlorous acid aqueous solution manufactured by the manufacturing method in Patent Literature 1 | 20 ppm | 0.65 | $1.4 \times 10^5$ | $2.9 \times 10^3$ | <300 | <300 | <300 |
| Chlorous acid aqueous solution A | 20 ppm | 0.59 | $3.6 \times 10^5$ | $1.5 \times 10^3$ | <300 | <300 | <300 |
| Chlorous acid aqueous solution preparation A | 20 ppm | 0.67 | $6.8 \times 10^6$ | $7.2 \times 10^4$ | <300 | <300 | <300 |
| Chlorous acid aqueous solution B | 20 ppm | 2.4 | <300 | <300 | <300 | <300 | <300 |
| Chlorous acid aqueous solution preparation B | 20 ppm | 2.4 | <300 | <300 | <300 | <300 | <300 |

The results for day 10 are shown.

TABLE 43

| Name of sample | pH | Chlorous acid concentration | Oxidation capability | Phenol coefficient |
|---|---|---|---|---|
| Chlorous acid aqueous solution manufactured by the manufacturing method in Pat. Literature 1 | 6.32 | 25192 ppm | 1406 | 13.3 |
| Chlorous acid aqueous solution A | 6.61 | 43929 ppm | 1514 | 12.2 |
| Chlorous acid aqueous solution preparation A | 6.14 | 4506 ppm | 142 | 1.3 |
| Chlorous acid aqueous solution B | 6.53 | 37846 ppm | 898 | 13.1 |
| Chlorous acid aqueous solution preparation B | 6.48 | 4650 ppm | 330.3 | 1.6 |

TABLE 44

| Name of sample | Chlorous acid concentration upon contact | Oxidation capability upon contact | Contact time to *E. coli* | | | | |
|---|---|---|---|---|---|---|---|
| | | | 15 sec | 30 sec | 1 min | 5 min | 10 min |
| Chlorous acid aqueous solution manufactured by the manufacturing method in Patent Literature 1 | 20 ppm | 1.12 | $2.0 \times 10^5$ | $3.2 \times 10^3$ | <300 | <300 | <300 |
| Chlorous acid aqueous solution A | 20 ppm | 0.69 | $3.1 \times 10^5$ | $1.8 \times 10^3$ | <300 | <300 | <300 |
| Chlorous acid aqueous solution preparation A | 20 ppm | 0.63 | $7.1 \times 10^6$ | $7.5 \times 10^4$ | <300 | <300 | <300 |
| Chlorous acid aqueous solution B | 20 ppm | 0.47 | $7.7 \times 10^6$ | $9.8 \times 10^6$ | $7.2 \times 10^6$ | $5.0 \times 10^4$ | <300 |
| Chlorous acid aqueous solution preparation B | 20 ppm | 1.42 | <300 | <300 | <300 | <300 | <300 |

The results for day 30 are shown.

TABLE 45

| Name of sample | pH | Chlorous acid concentration | Oxidation capability | Phenol coefficient |
|---|---|---|---|---|
| Chlorous acid aqueous solution manufactured by the manufacturing method in Pat. Literature 1 | 6.14 | 17016 ppm | 1186 | 11.2 |
| Chlorous acid aqueous solution A | 5.25 | 34191 ppm | 1347 | 10.1 |
| Chlorous acid aqueous solution preparation A | 6.14 | 4511 ppm | 138 | 1.2 |
| Chlorous acid aqueous solution B | 6.55 | 33162 ppm | 780 | 7.2 |
| Chlorous acid aqueous solution preparation B | 6.46 | 4580 ppm | 110 | 1.6 |

TABLE 46

| Name of sample | Chlorous acid concentration upon contact | Oxidation capability upon contact | Contact time to *E. coli* | | | | |
|---|---|---|---|---|---|---|---|
| | | | 15 sec | 30 sec | 1 min | 5 min | 10 min |
| Chlorous acid aqueous solution manufactured by the manufacturing method in Patent Literature 1 | 20 ppm | 1.39 | $1.1 \times 10^4$ | $1.8 \times 10^2$ | <300 | <300 | <300 |
| Chlorous acid aqueous solution A | 20 ppm | 0.79 | $2.9 \times 10^5$ | $2.0 \times 10^3$ | <300 | <300 | <300 |
| Chlorous acid aqueous solution preparation A | 20 ppm | 0.61 | $7.0 \times 10^6$ | $7.4 \times 10^4$ | $1.5 \times 10^3$ | <300 | <300 |
| Chlorous acid aqueous solution B | 20 ppm | 0.47 | $8.0 \times 10^6$ | $9.6 \times 10^6$ | $7.8 \times 10^6$ | $5.5 \times 10^4$ | <300 |
| Chlorous acid aqueous solution preparation B | 20 ppm | 0.48 | $7.8 \times 10^6$ | $6.9 \times 10^6$ | $6.2 \times 10^6$ | $4.5 \times 10^4$ | <300 |

Chlorous acid aqueous solution A manufactured by the present manufacturing method can be used to obtain aqueous solutions including various concentrations of chlorate as liquid by electrolysis, with salt as the raw material. Thus, chlorous acid aqueous solutions having more diverse chlorous acid concentrations and oxidation capability compared to chlorous acid aqueous solutions made by a conventional manufacturing method can be manufactured.

Since the primary active ingredient of chlorous acid aqueous solutions is chlorous acid, a chlorous acid aqueous solution manufactured by the manufacturing method patent in Patent Literature 1 is characterized by having an antimicrobial effect, sterilizing effect, microbe-removing effect, disinfecting effect, and antiviral effect having conventional functions. It was also found that chlorous acid aqueous solution A manufactured by the present manufacturing method and chlorous acid aqueous solution A maintaining a cyclic reaction by utilizing a buffer with this chlorous acid aqueous solution A as the raw material also exert an antimicrobial effect, sterilizing effect, microbe-removing effect, disinfecting effect, and antiviral effect having conventional features, just like a chlorous acid aqueous solution manufactured by the manufacturing method patent in Patent Literature 1.

Meanwhile, chlorous acid aqueous solution B and chlorous acid aqueous solution preparation B have a more highly reactive antimicrobial power, sterilizing power, microbe-removing power, disinfecting power, and antiviral power compared to chlorous acid aqueous solution A, enabling high reactivity to *E. coli* in 15 seconds of contact, which was impossible with conventional chlorous acid aqueous solutions.

While future research is required, this phenomenon is considered to be due to accelerated reaction rate from chlorous acid where chloride ions contained in first reaction gas are in an undissociated state to aqueous chlorine dioxide. As a result, high reactivity was imparted to the antimicrobial effect, sterilizing effect, microbe-removing effect, disinfecting effect, and antiviral effect that is slow and sustained due to a slow moving cyclic reaction.

As a reason thereof, mixing sodium hypochlorite and sodium chlorite under acidic conditions results in immediate decomposition into chlorate ions and chloride ions, such that the antimicrobial effect, sterilizing effect, microbe-removing effect, disinfecting effect, and antiviral effect are rapidly lost. In other words, the more distributable this mixture becomes, the more difficult it is to store the mixture in this state for a long period of time. For this reason, the mixture of sodium hypochlorite and sodium chlorite needs to be adjusted to strong alkaline pH for long term storage. In other words, the factor for stabilizing such a mixture is dependent on the pH. Accordingly, the high reactivity of chlorous acid aqueous solution B can maintain the antimicrobial power, sterilizing power, microbe-removing power, disinfecting power, and antiviral power in weak acidic region, so that it is evident that this is not an effect due to sodium hypochlorite.

In the result after 10 days, the antimicrobial power, sterilizing power, microbe-removing power, disinfecting power, and antiviral power of chlorous acid aqueous solution B significantly decreased, such that only the antimicrobial effect, sterilizing effect, microbe-removing effect, disinfecting effect, and antiviral effect with the same property as conventional chlorous acid aqueous solutions was exhibited.

On the other hand, even after 30 days, it was found that chlorous acid aqueous solution B had antimicrobial power, sterilizing power, microbe-removing power, disinfecting power, and antiviral power with high reactivity. In view of the above, it was found that not only the antimicrobial effect, sterilizing effect, microbe-removing effect, disinfecting effect, and antiviral effect of chlorous acid aqueous solutions with conventional features, but also antimicrobial effect, sterilizing effect, microbe-removing effect, disinfecting effect, and antiviral effect corresponding to high reactivity can be maintained for a long period of time by maintaining a cyclical reaction. In view of this result, the highly reactive antimicrobial effect, sterilizing effect, microbe-removing effect, disinfecting effect, and antiviral effect is not derived from sodium hypochlorite.

As disclosed above, the present invention is exemplified by the use of its preferred embodiments. However, it is understood that the scope of the present invention should be interpreted based solely on the Claims. The present application claims priority to Japanese Patent Application No. 2016-70264 (filed on Mar. 31, 2016). The entire content thereof is incorporated herein by reference. It is also understood that any patent, any patent application, and any references cited herein should be incorporated herein by reference in the same manner as the contents are specifically described herein.

INDUSTRIAL APPLICABILITY

In view of the above, an aqueous solution including a chlorous acid aqueous solution obtained by the present invention can be utilized in applications such as an antimicrobial agent, sterilizing agent, microbe-removing agent, disinfecting agent, antiviral agent, bleach, and blood stain removing agent.

The invention claimed is:

1. A method of manufacturing a chlorous acid aqueous solution, comprising the steps of:

(1) electrolyzing a salt to obtain a chlorate aqueous solution;
(2) generating a first reaction gas by adding at least one acid into the chlorate aqueous solution, wherein the first reaction gas comprises chlorine and chlorous acid; and
(3) generating a second reaction gas by adding hydrogen peroxide into the chlorate aqueous solution after the first reaction gas is no longer generated and capturing the second reaction gas by using a neutralization solution comprising hydrogen peroxide so as to obtain a chlorous acid aqueous solution, wherein the second reaction gas comprises chlorine dioxide and chlorous acid, and wherein only the second reaction gas captured by the neutralization solution is used for manufacturing the chlorous acid aqueous solution.

2. The method of claim 1, wherein the salt is sodium chloride.

3. The method of claim 2, wherein the sodium chloride meets the specification of sodium chloride in the $17^{th}$ edition of the Japanese Pharmacopoeia or a specification identical thereto.

4. The method of claim 1, wherein the chlorate or aqueous solution thereof comprises at least about 45% (w/v) sodium chlorate, and optionally comprises sodium hypochlorite or an unreacted salt.

5. The method of claim 1, wherein the electrolyzing comprises making an aqueous sodium chloride solution flow in a diaphragm-free electrolytic cell and adjusting a pH of an electrolyte solution to about 5.9 to about 7.5 while conducting electricity for about 15 hours or more under conditions with a voltage of about 2.75 to about 3.5 V, a current density of about 600 to about 5000 A/m2, and a solution temperature of about 70° C. to about 90° C., wherein the sodium chloride solution is saturated at room temperature.

6. The method of claim 5, wherein the voltage is about 3V.

7. The method of claim 5, wherein the current density is about 2500 A/m$^2$.

8. The method of claim 5, wherein the pH of the electrolyte solution is adjusted to about 5.9 to about 7.0.

9. The method of claim 8, wherein the pH of the electrolyte solution is adjusted to about 6.0.

10. The method of claim 1, wherein the at least one acid is selected from the group consisting of sulfuric acid, phosphoric acid, and nitric acid.

11. The method of claim 10, wherein a concentration of the sulfuric acid, phosphoric acid, or nitric acid is about 60% (w/w) to about 90% (w/w).

12. The method of claim 11, wherein the concentration of the sulfuric acid, phosphoric acid, or nitric acid is about 70% (w/w).

13. The method of claim 1, wherein the at least one acid is used with an acidic thiosulfuric acid or a salt thereof.

14. The method of claim 13, wherein a concentration of the acidic thiosulfuric acid is about 0% (w/v) to about 1.3% (w/v).

15. The method of claim 14, wherein the concentration of the acidic thiosulfuric acid is about 0.5% (w/v) to about 0.7% (w/v).

16. The method of claim 1, wherein an oxyacid with a reducing action is used concurrently with the at least one acid.

17. The method of claim 16, wherein the oxyacid with a reducing action is dithionous acid, peroxymonosulfuric acid, peroxydisulfuric acid, peroxyphosphoric acid, peroxychromic acid, manganese oxide, or acidic thiosulfuric acid.

18. The method of claim 17, wherein the oxyacid with a reducing action is dithionous acid or acidic thiosulfuric acid.

19. The method of claim 18, wherein the method comprises generating the oxyacid with a reducing action from a salt of the oxyacid with a reducing action.

20. The method of claim 19, wherein the salt of the oxyacid with a reducing action is dithionite, peroxymonosulfate, peroxydisulfate, peroxyphophate, peroxychromate, permanganate, or acidic thiosulfate.

21. The method of claim 20, wherein the salt of the oxyacid with a reducing action is sodium dithionite or sodium thiosulfate.

22. The method of claim 19, wherein the oxyacid with a reducing action is used concurrently with hydrogen peroxide.

23. The method of claim 22, wherein the oxyacid with a reducing action is dithionous acid or acidic thiosulfuric acid, wherein a weight concentration of the dithionous acid or acidic thiosulfuric acid is about 0.5 wt% to about 1.5 wt% when the dithionous acid or acidic thiosulfuric acid is used concurrently with hydrogen peroxide.

24. The method of claim 23, wherein the weight concentration of the dithionous acid or acidic thiosulfuric acid is about 0.5 wt% to about 1.0 wt%.

25. The method of claim 16, wherein the first reaction gas is generated via a first reaction in step (2) by adding an acid and the oxyacid with a reducing action.

26. The method of claim 25, wherein the second reaction gas is generated in step (3) by adding the hydrogen peroxide and the oxyacid with a reducing action when the first reaction is complete.

27. The method of claim 25, comprising the step of capturing the first reaction gas using a neutralization agent in step (2).

28. The method of claim 27, wherein a pH of the neutralization agent is about 6.0 or greater.

29. The method of claim 28, wherein the pH of the neutralization agent is about 10.3 to about 10.7.

30. The method of claim 28, wherein a total alkalinity (TAL) of the neutralization agent is about 20 or greater, wherein the TAL is measured by titrating 0.1 mol/L hydrochloric acid-standard acid solution until the sample has a pH of 4.0.

31. The method of claim 30, wherein a total alkalinity (TAL) of the neutralization agent is about 2000, wherein the TAL is measured by titrating 0.1 mol/L hydrochloric acid-standard acid solution until the sample has a pH of 4.0.

32. The method of claim 27, wherein the neutralization agent has a buffering power in a pH range of about 4.5 to about 7.5.

33. The method of claim 27, wherein the neutralization agent comprises any one of an inorganic acid, an inorganic acid salt, an organic acid, and an organic acid salt, or two or more types thereof.

34. The method of claim 1, further comprising the step of mixing any one of an inorganic acid, an inorganic acid salt, an organic acid, and an organic acid salt, or two or more types thereof, into the chlorous acid aqueous solution after the step (3).

35. The method of claim 1, further comprising the step of mixing any one of an inorganic acid and an inorganic acid salt, or two or more types thereof, into the chlorous acid aqueous solution after the step (3).

36. The method of claim 1, further comprising the step of mixing any one of an inorganic acid and an inorganic acid salt, or two or more types thereof, into the chlorous acid aqueous solution after the step (3), and then mixing any one of an inorganic acid, an inorganic acid salt, an organic acid, and an organic acid salt or two or more types thereof.

37. The method of claim 34, characterized in that the inorganic acid is carbonic acid, phosphoric acid, boric acid, or sulfuric acid.

38. The method of claim 34, characterized in that the inorganic acid salt is carbonate, bicarbonate, hydroxide salt, phosphate, or borate.

39. The method of claim 38, characterized in that the carbonate and bicarbonate is sodium carbonate, potassium carbonate, sodium bicarbonate, or potassium bicarbonate.

40. The method of claim 38, characterized in that the hydroxide salt is sodium hydroxide or potassium hydroxide.

41. The method of claim 38, characterized in that the phosphate is disodium hydrogen phosphate, sodium dihydrogen phosphate, trisodium phosphate, tripotassium phosphate, dipotassium hydrogen phosphate, or potassium dihydrogen phosphate.

42. The method of claim 38, characterized in that the borate is sodium borate or potassium borate.

43. The method of claim 33, characterized in that the organic acid is succinic acid, citric acid, malic acid, acetic acid, or lactic acid.

44. The method of claim 33, characterized in that the organic acid salt is sodium succinate, potassium succinate, sodium citrate, potassium citrate, sodium malate, potassium malate, sodium acetate, potassium acetate, sodium lactate, potassium lactate, or calcium lactate.

* * * * *